(12) United States Patent
Sriram et al.

(10) Patent No.: US 9,976,952 B2
(45) Date of Patent: May 22, 2018

(54) FLEXIBLE OR STRETCHABLE SENSOR FOR USE IN DETECTING A SUBSTANCE AND/OR ELECTROMAGNETIC RADIATION, AND A METHOD FOR DETECTING THEREOF

(71) Applicant: RMIT University, Melbourne (AU)

(72) Inventors: Sharath Sriram, Docklands (AU);
Madhu Bhaskaran, Docklands (AU);
Philipp Gutruf, Champaign, IL (US)

(73) Assignee: RMIT University, Melbourne (AU)

(*) Notice: Subject to any disclaimer, the term of this patent is extended or adjusted under 35 U.S.C. 154(b) by 0 days. days.

(21) Appl. No.: 15/173,272

(22) Filed: Jun. 3, 2016

(65) Prior Publication Data

US 2017/0350817 A1    Dec. 7, 2017

(51) Int. Cl.
| | | |
|---|---|---|
| *G01N 21/59* | (2006.01) | |
| *G01N 33/22* | (2006.01) | |
| *G01N 33/00* | (2006.01) | |
| *H01L 31/0296* | (2006.01) | |
| *H01L 31/0392* | (2006.01) | |
| *H01L 31/18* | (2006.01) | |
| *H01L 31/103* | (2006.01) | |

(52) U.S. Cl.
CPC ......... *G01N 21/59* (2013.01); *G01N 33/0037* (2013.01); *G01N 33/22* (2013.01); *H01L 31/0296* (2013.01); *H01L 31/03926* (2013.01); *H01L 31/1032* (2013.01); *H01L 31/1828* (2013.01); *G01N 2201/02* (2013.01)

(58) Field of Classification Search
CPC ............... G01N 21/59; G01N 2201/02; G01N 33/0037; G01N 33/22; H01L 31/0296; H01L 31/03926; H01L 31/1032; H01L 31/1828
See application file for complete search history.

(56) References Cited

U.S. PATENT DOCUMENTS

2016/0169824 A1* 6/2016 Shin ..................... G01N 27/127
73/31.06

OTHER PUBLICATIONS

Gutruf, Philipp "Visible-Blind UV Imaging with Oxygen-Deficient Zinc Oxide Flexible Devices," Advance Electronic Materials, 2015; vol. 1.

(Continued)

*Primary Examiner* — Mark R Gaworecki
(74) *Attorney, Agent, or Firm* — Hovey Williams LLP

(57) ABSTRACT

In general, this disclosure is directed to a flexible or stretchable sensor and a method of detecting a substance and/or electromagnetic radiation using said sensor. The sensor comprises a flexible or stretchable substrate, a pair of terminal electrodes disposed on the flexible or stretchable substrate in mutually spaced apart and opposing relation, and a sensing element applied to the flexible or stretchable substrate, between and in electrical contact with the pair of terminal electrodes, wherein the sensing element is responsive to a substance and/or electromagnetic radiation impinging thereon, and wherein when a voltage is applied across the sensor, an electrical signal is generated that is proportional to a resistance value corresponding to a sensing of the substance and/or electromagnetic radiation impinging on the sensing element.

35 Claims, 15 Drawing Sheets
(14 of 15 Drawing Sheet(s) Filed in Color)

(56) References Cited

OTHER PUBLICATIONS

Gutruf, Philipp "Stretchable and Tunable Microtectonic ZnO-Based Sensors and Photonics," Small Journal, 2015, pp. 4532-4539; vol. 11, No. 35.
Gutruf, Philipp, Supporting Information for Advance Electronic Materials, "Visible-Blind UV Imaging with Oxygen-Deficient Zinc Oxide Flexible Devices," 2015.
Gutruf, Philipp, Supporting Information for Small, "Stretchable and Tunable Microtectonic ZnO-Based Sensors and Photonics" 2015.
Chung, Hyun-Joong "Ultrathin, Stretchable, Multiplexing pH Sensor Arrays on Biomedical Devices With Demonstrations on Rabbit and Human Hearts Undergoing Ischemia," Adv. Health Mater, Jan. 2014, pp. 59-68, vol. 3(1).
Hwang, Suk-Won, "A Physically Transient Form of Silicon Electronics, With Integrated Sensors, Actuators and Power Supply," Science, Sep. 28, 2012, pp. 1640-1644; vol. 337 (6102).
Yan, He, "A high-mobility electron-transporting polymer for printed transistors," Nature , Feb. 5, 2009, vol. 457, Macmillan Publishers Limited.
Gustafsson, G, "Flexible light-emitting diodes made from soluble conducting polymers," Nature, Jun. 11, 1992, vol. 357.
Gelinck, Gerwin H. "Flexible active-matrix displays and shift registers based on solution-processed organic transistors," Jan. 25, 2004.
Yagi, Iwao, "A flexible full-color AMOLED display driven by OTFTs," Journal of the SID, 2008, vol. 16(1).
Sun, Lei, "12-GHz Thin-Film Transistors on Transferrable Silicon Nanomembranes for High-Performance Flexible Electronics," Small, Sep. 27, 2010, pp. 2553-2557, vol. 6 (22).
Kim, Jeonghyun, "Epidermal Electronics with Advanced Capabilities in Near-Field Communication," Small, 2015, pp. 906-912, vol. 11(8).
Akyildiz, I.F. "Wireless sensor networks: a survey" Computer Networks, 2002, pp. 393-422, vol. 38.
Walia, Sumeet, "Transition metal oxides—Thermoelectric properties," Progress in Material Science, 2013, pp. 1443-1489, vol. 58.
Gutruf, Philipp, "Transparent functional oxide stretchable electronics: micro-tectonics enabled high strain electrodes," NPG Asia Materials, 2013, vol. 5, Nature Publishing Group.
Nyberg, Mats, "Hydrogen Dissociation on Reconstructed ZnO Surfaces," J. Phys. Chem. 1996, pp. 9054-9063, vol. 100 (21).
McAlpine, Michael C, "Highly ordered nanowire arrays on plastic substrates for ultrasensitive flexible chemical sensors," Nature Materials, Apr. 22, 2007, Nature Publishing Group.
Sberveglieri, G. "Recent developments in semiconducting thin-film gas sensors," Sensors and Actuators, 1995, pp. 103-109.
Wang, H. T. "Hydrogen-selective sensing at room temperature with ZnO nanorods," Applied Physics Letters, 2005, vol. 86.
Breedon, M. "Adsorption of NO2 on Oxygen Deficient ZnO(2110) for Gas Sensing Applications: A DFT Study," J. Phys. Chem., 2010, pp. 16603-16610, vol. 114.
Shishiyanu, Sergiu T. "Sensing characteristics of tin-doped ZnO thin films as NO2 gas sensor," Sensors and Actuators, 2007, pp. 379-386, vol. 107.
Hu, Guofeng, "Piezotronic effect enhanced Schottky-contact ZnO micro/nanowire humidity sensors," Nano Research, 2014, pp. 1083-1091, vol. 7 (7).
Zhou, Ranran, "Piezotronic effect enhanced detection of flammable/toxic gases by ZnO micro/nanowire sensors," Nano Energy, Feb. 2, 2015, pp. 588-596, vol. 12.
Pan, Caofeng, "Piezotronic Effect on the Sensitivity and Signal Level of Schottky Contacted Proactive Micro/Nanowire Nanosensors," Acs Nano, 2013, pp. 1803-1810, vol. 7 (2).
Yu, Ruomeng, "Enhanced performance of GaN nanobelt-based photodetectors by means of piezotronic effects," Nano Research 2013, pp. 758-766; 6 (10).
Heiland, G, "Homogeneous Semiconducting Gas Sensors," Sensors and Actuators, 1982, pp. 343-361, vol. 2.

Rezakazemi, Mashallah, "Hydrogen separation and purification using crosslinkable PDMS/zeolite A nanoparticles mixed matrix membranes," International Journal of Hydrogen Energy, 2012, pp. 14576-14589, vol. 37.
Jun, Jin Hyung, "Ultraviolet photodetectors based on ZnO nanoparticles," Ceramics International, Apr. 15, 2009, pp. 2797-2801, vol. 35.
Zhang, D H "Fast photoresponse and the related change of crystallite barriers for ZnO films deposited by RF sputtering," J. Phys. D. Appl. Phys. Feb. 15, 1995, pp. 1273-1277, vol. 28.
Kind, Hannes, "Nanowire Ultraviolet Photodetectors and Optical Switches," Advanced Materials, Jan. 16, 2002, vol. 14 (2).
Qi, Junjie, "A self-powered ultraviolet detector based on a single ZnO microwire/p-Si film with double heterojunctions," The Royal Society of Chemistry, Nanoscale, 2014 pp. 6025-6029, vol. 6.
Bai, Zhiming, "Ultraviolet and visible photoresponse properties of a ZnO/Si heterojunction at zero bias," The Royal Society of Chemistry, RSC Adv., 2013 pp. 17682-17688, vol. 3.
Lin, Pei, "Enhanced photoresponse of Cu2O/ZnO heterojunction with piezo-modulated interface engineering," Nano Research, 2014, pp. 860-868, vol. 7 (6).
Zheng, Xin, "Tunable channel width of a UV-gate field effect transistor based on ZnO micro-nano wire,"Royal Society of Chemistry, RSC Advances, Apr. 4, 2014, pp. 18378-18381, vol. 4.
Soci, C. "ZnO Nanowire UV Photodetectors with High Internal Gain," Nano Letters, Feb. 26, 2007, pp. 1003-1009, vol. 7 (4).
Lin, Pei, "Self-Powered UV Photosensor Based on PEDOT:PSS/ZnO Micro/Nanowire with Strain-Modulated Photoresponse," Acs Applied Materials & Interfaces, Mar. 26, 2013, pp. 3671-3676, vol. 5.
Ghosh, R. "Effect of substrate-induced strain on the structural, electrical, and optical properties of polycrystalline ZnO thin films," Journal of Applied Physics, Sep. 1, 2004, vol. 96 (5).
Becheri, Alessio, "Synthesis and characterization of zinc oxide nanoparticles: application to textiles as UV-absorbers," J Nanopart Res, Oct. 30, 2007, pp. 679-689, vol. 10.
Vengsarkar, Ashish, "Long-Period Fiber Gratings as Band-Rejection Filters," Journal of Lightwave Technology, Jun. 2007, pp. 58-65, vol. 14 (1).
Goodno, Gregory, "Ultrafast heterodyne-detected transient-grating spectroscopy using diffractive optics," J. Opt. Soc. Am. B., Jun. 1998, pp. 1791-1794, vol. 15 (6).
Ma, Teng, "Micro-strain sensing using wrinkled stiff thin films on soft substrates as tunable optical grating," Optical Society of America, May 20, 2013, vol. 21 (10).
Ellmer, Klaus, "Magnetron sputtering of transparent conductive zinc oxide: relation between the sputtering parameters and the electronic properties," J. Phys. D: Appl. Phys., 2000, pp. 17-32, vol. 33.
Xiong, Gang, "Control of p- and n-type conductivity in sputter deposition of undoped ZnO," Applied Physics Letters, Feb. 18, 2002, vol. 80 (7).
Lefever, R. A. "Flame Fusion Growth of C-Type Rare-Earth Oxides," Review of Scientific Instruments, 1962, pp. 1470-1471, vol. 33.
Bie, Li-Jian, "Nanopillar ZnO gas sensor for hydrogen and ethanol," Sensors and Actuators B, 2007, pp. 604-608, vol. 126.
Kappertz, O. "Reactive sputter deposition of zinc oxide: Employing resputtering effects to tailor film properties," Thin Solid Films, May 13, 2005, pp. 64-67, vol. 484.
Zhang, Dongping, "Properties of ZnO thin films deposited by DC reactive magnetron sputtering under different plasma power," Applied Physics A, 2009, pp. 437-441, vol. 97.
Xu, Yibin, "Thermal conductivity of ZnO thin film produced by reactive sputtering," Journal of Applied Physics, 2012, vol. 111.
Swain, Pradyumna, "Curved CCD Detector Devices and Arrays for Multi-Spectral Astrophysical Applications and Terrestrial Stereo Panoramic Cameras," Proc. of SPIE, 2004, vol. 5499 http://proceedings.spiedigitallibrary.org/ on Aug. 30, 2016 Terms of Use: http://spiedigitallibrary.org/ss/termsofuse.aspx.
Grayson, Timothy P., "Curved Focal Plane Wide Field of View Telescope Design," Proceedings of SPIE, 2002, vol. 4849, http://proceedings.spiedigitallibrary.org/ on Aug. 30, 2016 Terms of Use: http://spiedigitallibrary.org/ss/termsofuse.aspx.

(56) References Cited

OTHER PUBLICATIONS

Ko, Heung Cho, "A hemispherical electronic eye camera based on compressible silicon optoelectronics," Nature, Aug. 7, 2008, vol. 454.
Razeghi, M. "Semiconductor ultraviolet detectors," Journal of Applied Physics, May 15, 1996, vol. 79 (10).
Sheng, Xing, "Silicon-Based Visible-Blind Ultraviolet Detection and Imaging Using Down-Shifting Luminophores," Advanced Optical Materials, 2014, pp. 314-319, vol. 2.
Walker, D. "Visible blind GaN p-i-n photodiodes," Applied Physics Letters, Jun. 22, 1998, vol. 72 (25).
Mckeag, Robert D. "Diamond UV photodetectors: sensitivity and speed for visible blind applications," Diamond and Related Materials, 1998, pp. 513-518, vol. 7.
Du, Xiaolong, "Controlled Growth of High-Quality ZnO-Based Films and Fabrication of Visible-Blind and Solar-Blind Ultra-Violet Detectors," Advance Materials, 2009, pp. 4625-4630, vol. 21.
Nasiri, Noushin, "Ultraporous Electron-Depleted ZnO Nanoparticle Networks for Highly Sensitive Portable Visible-Blind UV Photodetectors," Advanced Materials, 2015, pp. 4336-4343, vol. 27.
Gedamu, Dawit, "Rapid Fabrication Technique for Interpenetrated ZnO Nanotetrapod Networks for Fast UV Sensors," Advance Materials, 2014, pp. 1541-1550, vol. 26.
Prasad, Muvva Durga, "Low temperature growth of ZnO nanostructures on flexible polystyrene substrates for optical, photoluminescence and wettability applications," Materials Research Express, May 8, 2016, vol. 3.
Lim, B.W. "8×8 GaN Schottky barrier photodiode array for visible-blind imaging," Electronics Letters, Mar. 27, 1997, vol. 33 (7).
Long, J.P. "UV detectors and focal plane array imagers based on AlGaN p-i-n photodiodes," Opto-Electronics Review, 2002, vol. 10 (4).
McClintock, R. "320×256 solar-blind focal plane arrays based on $Al_xGa_{1-x}N$," Applied Physics Letters, 2005, vol. 86.
Song, Jizhong, "Transparent Electrodes Printed with Nanocrystal Inks for Flexible Smart Devices," Angew. Chem. Int. Ed. 2015, pp. 9760-9774, vol. 54.
Gutruf, Philipp, "Stretchable and Tunable Microtectonic ZnO-Based Sensors and Photonics," Small Journal, 2015, pp. 4532-4539, vol. 35.
Gutruf, Philipp, "Strain response of stretchable micro-electrodes: Controlling sensitivity with serpentine designs and encapsulation," Applied Physics Letters, Jan. 15, 2014, vol. 104.
Lu, Nanshu, "Metal films on polymer substrates stretched beyond 50%," Applied Physics Letters, 2007, vol. 91.
Liu, Kewei, "ZnO-Based Ultraviolet Photodetectors," Sensors, 2010, vol. 10.
Nakano, M. "Transparent polymer Schottky contact for a hight performance visible-blind ultraviolet photodiode based on ZnO," Applied Physics Letters, 2008, vol. 93 (12).
Liu, Y. "Ultraviolet Detectors Based on Epitaxial ZnO Films Grown by MOCVD," Journal of Electronic Materials, 2000, vol. 29 (1).
Gutruf, Philip "Visible-Blind UV Imaging with Oxygen-Deficient Zinc Oxide Flexible Devices," Advance Electronic Materials, 2015, vol. 1.

\* cited by examiner

FLEXIBLE OR STRETCHABLE SENSOR FOR USE IN DETECTING A SUBSTANCE AND/OR ELECTROMAGNETIC RADIATION, AND A METHOD FOR DETECTING THEREOF

FIELD OF THE INVENTION

The present invention relates to sensors and in particular to a flexible or stretchable sensor for use in detecting a substance and/or electromagnetic radiation and a method for the detection thereof.

The invention has been developed primarily for use in detecting the presence of a substance such as a hazardous gas or liquid and/or detecting ultra-violet (UV) radiation and will be described hereinafter with reference to these applications. However, it will be appreciated that the invention is not limited to this particular field of use.

The following discussion of the background to the invention is intended to facilitate an understanding of the invention. However, it should be appreciated that the discussion is not an acknowledgement or admission that any of the material referred to was published, known or part of the common general knowledge in Australia or any other country as at the priority date of any one of the claims of this specification.

BACKGROUND OF THE INVENTION

The concept of realizing electronic applications on flexible, particularly elastically stretchable, 'skins' that conform to irregularly-shaped surfaces is revolutionizing fundamental research into mechanics and materials that can enable high performance stretchable and flexible electronic devices. Such stretchable and flexible electronic devices are expected to find wide application in the field of wearable electronic devices, and the like. It is widely believed that the ability to operate such stretchable and flexible electronic devices under various mechanically-stressed states will provide a set of unique functionalities that are beyond the capabilities of conventional rigid electronics.

Owing to rapid development in recent years, some mechanically deformable devices have been demonstrated to operate almost at par with their rigid counterparts in consumer applications such as organic LEDs,[1] stretchable displays,[2,3] and high-speed transistors,[4] as well as devices operating on the epidermis.[5] However, the wide reach of this technology is still yet to be fully exploited.

For instance, flexible sensors capable of sensing chemical or biological substances, particularly gases, would be useful in the event a person has to venture into a potentially hazardous environment. However, the realization of a flexible gas sensor that can operate at room temperature to enable the detection of a gas at low concentration is still very much in its infancy.[6] Indeed, most gas sensors, even on rigid platforms, are required to operate at elevated temperatures of several hundred degrees Celsius.[7]

In the case of imaging systems for sensing electromagnetic radiation, particularly ultra-violet (UV) radiation, these systems are typically fabricated on rigid planar substrates on account of the demanding requirements on the detectors in terms of high dynamic range, low noise, high speed, and high resolution, and the limitations associated with the optical elements used in such imaging systems. However, when comparing such planar electronic imaging devices such as CMOS sensors to biological imaging systems such as the human eye, these rigid imaging sensors invariably lack the performance, especially when comparing field of view and aberrations,[8] due to their inherent flat design.[9]

It is widely believed that by curving the plane of the sensing element so as to mimic the human eye, this would reduce the distortion and chromatic aberration significantly, thereby improving the performance of such imaging systems. This would be especially important for imaging at non-visible wavelengths such as the UV A and B regime, due to the low availability and high cost of suitable optics. In this respect, readily available, low complexity devices with flexible characteristics would be favourable for applications such as imaging of visible-blind UV radiation for monitoring of sterilisation, lithography, flame detection, environmental studies and military applications.[1]

While there is a significant need for flexible sensors capable of detecting substances and/or electromagnetic radiation with sufficient sensitivity to be effective in the field of say, wearable electronic devices, there are clearly limitations that present a significant barrier to the realisation of such flexible sensors.

The present invention seeks to provide a flexible or stretchable sensor for use in detecting a substance and/or electromagnetic radiation and a method for the detection thereof, which will overcome or substantially ameliorate at least some of the deficiencies of the prior art, or to at least provide an alternative.

SUMMARY OF THE INVENTION

According to a first aspect of the present invention, there is provided a flexible or stretchable sensor for use in detecting a substance and/or electromagnetic radiation, the sensor comprising: a flexible or stretchable substrate; a pair of terminal electrodes disposed on the flexible or stretchable substrate in mutually spaced apart and opposing relation; and a sensing element applied to the flexible substrate, between and in electrical contact with the pair of terminal electrodes, wherein the sensing element is responsive to a substance and/or electromagnetic radiation impinging thereon, and wherein when a voltage is applied across the sensor, an electrical signal is generated that is proportional to a resistance value corresponding to a sensing of the substance and/or electromagnetic radiation impinging on the sensing element.

In a preferred embodiment, the sensing element comprises an oxygen-deficient metal oxide layer defining a sensor surface oriented for contact with the substance and/or electromagnetic radiation in use.

In one embodiment, the sensor surface of the oxygen-deficient metal oxide layer comprises a micro-tectonic plate-like structure.

Suitably, the micro-tectonic plate-like structure allows the oxygen-deficient metal oxide layer to flex or stretch when the sensor is subject to an applied force.

In one embodiment, the sensor surface of the oxygen-deficient metal oxide layer has an average surface roughness that falls within a range of about 40 nm to about 170 nm.

Suitably, the oxygen-deficient metal oxide layer is formed from a metal oxide selected from the group consisting of zinc oxide (ZnO), indium tin oxide (ITO), tin oxide and titanium dioxide.

In one embodiment, the oxygen deficient metal oxide layer has a thickness that falls within a range of about 10 nm to about 1 μm.

In one embodiment, the sensing element further comprises a polymer isolation layer comprising a plurality of cavities into which the oxygen-deficient metal oxide layer is embedded.

Suitably, the polymer isolation layer is selected from the group consisting of polyimide (PI), polymethyl methacrylate (PMMA), photo-patternable epoxy resin and polyethylene terephthalate (PET).

In a preferred embodiment, the flexible or stretchable substrate comprises a polymer or elastomer.

Suitably, the polymer or elastomer is selected from the group consisting of polydimethylsiloxane (PDMS), polyimide (PI) and polyethylene terephthalate (PET).

In one embodiment, the polymer or elastomer is a bioinert or biocompatible material.

In one embodiment, the polymer or elastomer is a gas-permeable material.

In one embodiment, the polymer or elastomer has a thickness that falls within a range of about 10 µm to about 500 µm.

Preferably, the sensing element is caused to flex or stretch when the sensor is subject to an applied force.

In one embodiment, the applied force is selected from the group consisting of a stretching force, a compressive force, a twisting force and a bending force.

Suitably, the force applied to the sensor in use falls within a range of about −5% to about 15% of strain.

Preferably, the substance detected by the sensing element is a gas or a liquid.

In one embodiment, the substance detected by the sensing element is a gas selected from the group consisting of $H_2$, $NO_2$, $SF_6$ and $C_4H_{10}$.

In one embodiment, the gas detected by the sensing element is $H_2$ with a sensitivity to $H_2$ concentrations of less than 1% $H_2$ in air balance with a flow rate of 200 sccm.

In one embodiment, the gas detected by the sensing element is $NO_2$ with a sensitivity to $NO_2$ concentrations of less than 9.9 parts per million of $NO_2$ in zero air at a flow rate of 200 sccm.

In one embodiment, the substance detected by the sensing element is a liquid selected from the group consisting of gasoline and $C_2H_5OH$.

Suitably, the substance or electromagnetic radiation detected by the sensing element is detected at a temperature that falls within a range of 20 degrees Centigrade to 50 degrees Centigrade.

Preferably, the substance or electromagnetic radiation detected by the sensing element has a wavelength that falls within a range of 200 nm to 400 nm.

According to a second aspect of the present invention, there is provided a method of detecting a substance and/or electromagnetic radiation using a flexible or stretchable sensor, the method comprising the steps of: contacting a sensing element of a flexible or stretchable sensor according to the first aspect with a substance and/or electromagnetic radiation; applying a voltage across the sensor; and detecting an electrical signal generated that is proportional to a resistance value corresponding to a sensing of the substance and/or electromagnetic radiation impinging on the sensing element.

In one embodiment, the sensing element is caused to flex or stretch when the sensor is subject to an applied force.

Preferably, the applied force is selected from the group consisting of a stretching force, a compressive force, a twisting force and a bending force.

Suitably, the force applied to the flexible sensor in use falls within a range of about 4% to about 15% of strain.

Preferably, the substance detected by the sensing element is a gas or a liquid.

In one embodiment, the gas is selected from the group consisting of $H_2$, $NO_2$, $SF_6$ and $C_4H_{10}$.

In one embodiment, the gas detected by the sensing element is $H_2$ with a sensitivity to $H_2$ concentrations of less than 1% $H_2$ in an air balance with a flow rate of 200 sccm.

In one embodiment, the gas detected by the sensing element is $NO_2$ with a sensitivity to $NO_2$ concentrations of less than 9.9 parts per million in zero air at a flow rate of 200 sccm.

In one embodiment, the substance detected by the sensing element is a liquid selected from the group consisting of gasoline and $C_2H_5OH$.

Preferably, the electromagnetic radiation detected by the sensing element has a wavelength that falls within a range of 200 nm to 400 nm.

Preferably, one or more of steps a) to c) is conducted at a temperature that falls within a range of 20 degrees Centigrade to 50 degrees Centigrade.

Other aspects of the invention are also disclosed

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Notwithstanding any other forms which may fall within the scope of the present invention, preferred embodiments of the invention will now be described, by way of example only, with reference to the accompanying drawings in which.

DETAILED DESCRIPTION OF SPECIFIC EMBODIMENTS

Figure 1:
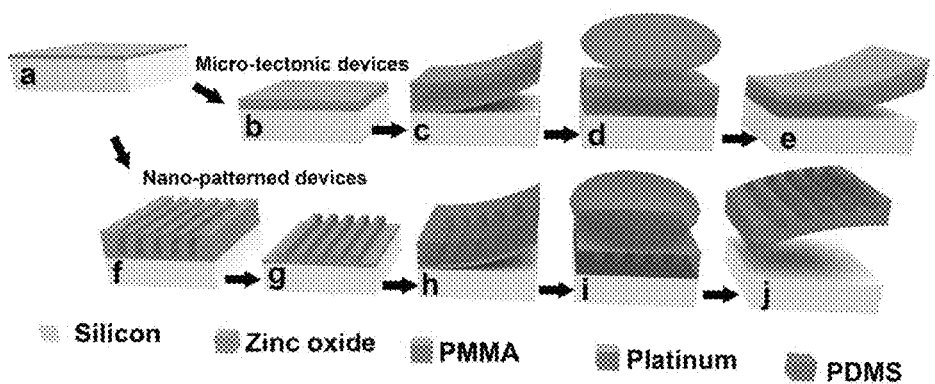
FIG. 1 shows a schematic representation of a method of manufacturing a stretchable micro-tectonic oxygen-deficient ZnO-based sensor (ZnO/PDMS) [steps (a) to (e)] and a stretchable nano-patterned oxygen-deficient ZnO-based sensor [steps (f) to (j)] in accordance with a preferred embodiment of the present invention.

It should be noted in the following description that like or the same reference numerals in different embodiments denote the same or similar features.

The present invention is predicated on the finding of fabricating flexible or stretchable, transparent and ultra-portable sensors and a method of detecting a substance and/or electromagnetic radiation using said flexible or stretchable sensors in order to realise functional, transparent electronic devices.

It will be understood by persons or ordinary skill in the relevant art that the term "flexible" refers to a material that is capable of undergoing strain, such as bending, without adverse impact of physical characteristics, such as irreversible break-down associated with material fracture, for example. Similarly, it will also be understood that the term "stretchable" is used in a similar manner but refers to strain larger than strain occurring during bending, typically higher than 4%, to refer to reversible strain without material fracture.

"Strain" is defined as: $\in = \Delta L/L$ for lengths changed from L (at rest) to L+$\Delta$L (under an applied force), where $\Delta$L is the displacement distance from resting. Uniaxial strain refers to a force applied to an axis of the substrate to generate the displacement $\Delta$L. Strain is also generated by forces applied in other directions, such as a bending force, a compressive force, a shearing force, and any combination thereof. Strain or compression may also be generated by stretching a curved surface to a flat surface, or vice versa. "Level of strain" refers to the magnitude of the strain and can range from negative (corresponding to compression) to zero (relaxed state) to positive (corresponding to elongation or stretching). Strain is related to a material's "Young's modulus" and applied stress. Young's modulus is a mechanical property of a material, device or layer which refers to the ratio of stress to strain for a given substance.

Stretchable Sensor

A stretchable sensor for use in detecting a substance and/or electromagnetic radiation according to a preferred embodiment of the present invention will now be described.

In its simplest form, the stretchable sensor comprises a stretchable substrate and a sensing element applied to the stretchable substrate that is responsive to a substance and/or electromagnetic radiation. The sensing element comprises a metal oxide layer that when applied to the stretchable substrate, defines a sensor surface that is oriented away from the stretchable substrate for contact with the substance and/or electromagnetic radiation in use. Metal oxides are attractive candidates as functional materials for a variety of electronic and optoelectronic applications. Their electronic properties can range from insulating to semiconducting and can be readily tuned by morphological and stoichiometric alterations.[10] Additionally, their carrier transport properties are well-understood and various engineering processes are well-established for manipulating them.

The metal oxide layer may be produced using any suitable metal oxide selected from the group consisting of zinc oxide (ZnO), indium tin oxide (ITO), tin oxide and titanium dioxide.

In a preferred form, the metal oxide layer is an oxygen-deficient metal oxide layer formed from a metal oxide selected from the group consisting of zinc oxide (ZnO) and indium tin oxide (ITO). And as will be described below, the inventors have found that good results may be obtained when the metal oxide layer is an oxygen-deficient zinc oxide (ZnO) layer.

The inventors believe that by incorporating an oxygen-deficient ZnO thin film onto a stretchable platform, this offers a potential for designing a wide variety of tunable, stretchable sensing platforms (with the added benefit of optical transparency or translucency).

Thus, for the purpose of demonstrating the effectiveness of the stretchable sensor as a high performance sensing device suited for the detection of a substance and/or electromagnetic radiation, oxygen-deficient ZnO is therefore chosen as the representative functional oxide due to the well-established versatility of its electronic and optical characteristics, susceptibility to modulation via a variety of stimuli, and bio-compatibility.

To overcome the technological difficulties that are encountered in the fabrication of such sensor devices, the inventors have implemented a transfer technique presented in a previous work.[11] The process relies on the poor adhesion of platinum to silicon which allows high temperature oxide thin films to be deposited and defined with standard micro-fabrication techniques and subsequently peeled-off using PDMS. This method was adapted for ZnO and for nanoscale features, as depicted in FIG. 1.

Manufacturing Method

Referring specifically to FIG. 1, the schematic representation shows a method of manufacturing a large area stretchable ZnO-based sensor [steps (a) to (e)] and a nano-patterned stretchable ZnO-based sensor [steps (f) to (j)].

In the case of the large area stretchable ZnO-based sensor, the method comprises as a first step (a) the step of depositing a platinum layer, with no adhesion promoter onto the surface of a silicon wafer. The platinum layer may be of any suitable thickness to ensure a uniformly thick film. In one embodiment, the platinum layer is at least 50 nm thick.

In step (b), an oxygen-deficient zinc oxide thin film is sputter-deposited on top of the platinum layer at 250° C. The as-deposited oxygen-deficient ZnO layer may be of any suitable thickness to suit the desired application.

In one embodiment, the oxygen-deficient ZnO layer has a thickness that falls within the range of about 10 nm to about 1 µm.

In step (c), a suitable polymer is spun-on top of the oxygen-deficient zinc oxide layer and then cured so as to form the stretchable substrate part of the oxygen-deficient ZnO-based stretchable sensor. A suitable polymer or elastomer is one which is stretchable when cured, and in the case where the sensor is to be used as a wearable electronic device, bioinert or biocompatible. In this respect, the polymer or elastomer may be selected from any one of the following group consisting of, but not limited to: polydimethylsiloxane (PDMS), polyimide (PI) and polyethylene terephthalate (PET).

In the case where stretchability is highly desired, such as in the manufacture of a wearable, skin-mounted electronic device, then the inventors have found that PDMS is a suitable biocompatible elastomer. Indeed, good results have been obtained when PDMS is deposited at a thickness that falls within a range of about 10 µm to about 500 µm. It will be appreciated by persons of ordinary skill in the art however, that the choice of polymer thickness is not limited to the aforementioned range, but rather the thickness may, at least in part, be dictated by the application to which the stretchable oxygen-deficient ZnO-based sensor is to be used.

Once the PDMS has cured, the combined layered structure is then peeled off the silicon wafer on account of the poor adhesion of the platinum layer to the silicon wafer surface.

In step (d), the layered structure is inverted and applied to the surface of the same, or another silicon wafer, and the now exposed platinum layer is removed from the layered structure by reactive ion etching (RIE).

Once all the platinum has been removed, the completed stretchable ZnO-based sensor is released from the silicon wafer in accordance with step e).

Figure 2:
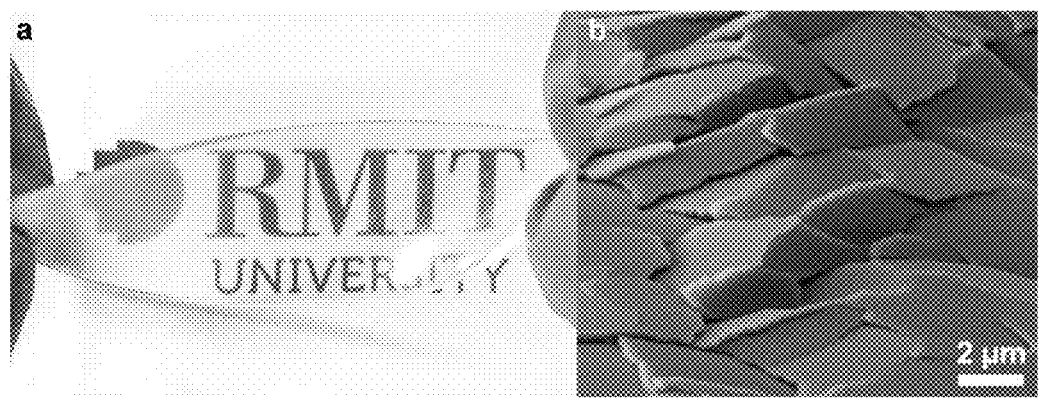
FIG. 2 shows (a) an image demonstrating the transparency and flexibility of the micro-tectonic oxygen-deficient ZnO-based sensor (ZnO/PDMS) of FIG. 1, and (b) a false-colour scanning electron micrograph of a surface of the micro-tectonic oxygen-deficient ZnO-based sensor (ZnO/PDMS) of FIG. 1.

FIG. 2(a) shows a photograph of the as-formed large area stretchable ZnO-based sensor (without electrodes) produced according to the above method. The photograph reveals the transparency of the as-formed ZnO-based sensor as well as its flexibility.

FIG. 2(b) shows a false-colour scanning electron micrograph of the surface-cracked micro-tectonic plate-like morphology of the surface of the ZnO-based sensor. The inventors have previously found that the micro-tectonic phenomenon governs the stretchability of the thin oxide films.[11] This phenomenon occurs when thin, brittle oxide films are incorporated into elastomeric films, the brittle oxide layer forms micrometer-sized plates which overlap and slide over each other. Moreover, due to the high adhesion between the oxygen-deficient ZnO thin film and the PDMS, an electrical contact is maintained between the individual ZnO micro-tectonic plates which combine to form one large functional surface.

In the case of the nano-patterned stretchable ZnO-based sensor, the method comprises as a first step (f), the step of applying a thick layer of polymethyl methacrylate (PMMA) on to the platinum layer and then using electron-beam lithography to define nano-patterned features in the PMMA. Following immersion in MIBK developer to develop the nano-pattern, an oxygen-deficient zinc oxide thin film is then sputter deposited on top of the nano-patterned structure at 250° C. In a similar fashion to the large area stretchable micro-tectonic ZnO-based sensor described above, the as-deposited oxygen-deficient ZnO thin film has a thickness that falls within the range of about 10 nm to about 500 nm.

In step (g), excess ZnO is then lifted-off in acetone.

Step (h) is conducted according in a similar manner to step (c) above in that a suitable polymer such as PDMS is spun on top of the nano-patterned structure and then cured, such that the ZnO nanostructures are now embedded within the PDMS.

Once cured, the combined layered structure is peeled off the silicon wafer. Here, the cured PDMS acts as the stretchable substrate for the resulting nano-patterned stretchable ZnO-based sensor. The inventors have again found that good results are obtained when PDMS has been deposited at a thickness that falls within a range of about 10 µm to about 500 µm.

In step (i), the layered structure is inverted and applied to the surface of the same, or another silicon wafer, and the now exposed platinum layer is removed from the layered structure by reactive ion etching (RIE).

Once all the platinum has been removed, the completed stretchable nano-patterned ZnO-based sensor is released from the silicon wafer in accordance with step (j). Specific details on the conditions employed in the above manufacturing method process are given in the Experimental Section below.

The inventors have found that this ubiquitous technique allows the creation of transparent, stretchable devices with nanometer resolution as well as large area functional devices without the need of tailoring the production method to the design.

Characterisation

Figure 3:
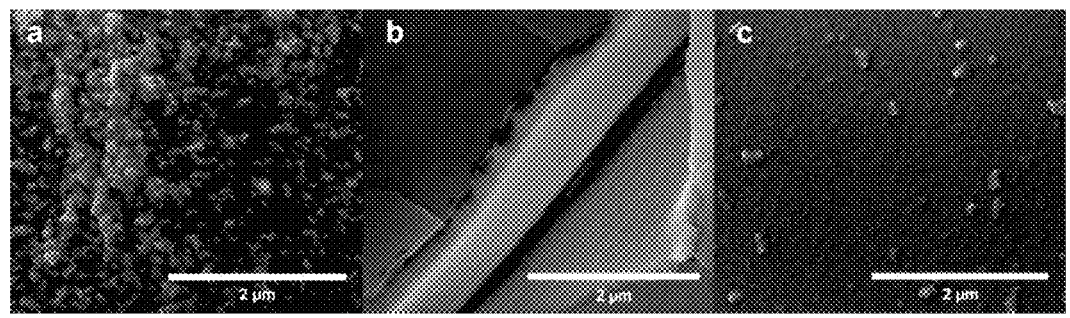
FIG. 3 shows a comparison of surface morphologies of ZnO thin films sputter-deposited on: (a) polyimide, (b) transferred onto polydimethylsiloxane (PDMS), and (c) silicon, as imaged using scanning electron microscopy (scale=2 µm)

FIG. 3 shows a comparison of the surface morphology of oxygen-deficient ZnO thin films formed on three different substrates: (a) polyimide, (b) PDMS, and (c) silicon. The silicon and polyimide samples were imaged under high vacuum, while the PDMS sample was imaged in a low vacuum mode at a pressure of 0.6 Torr. It is seen that the film surface is rougher when the oxygen-deficient ZnO thin film is deposited on the elastomeric substrates.

To further verify this observation, a line segment on each surface was profiled to investigate the macroscopic surface roughness.

Figure 4:
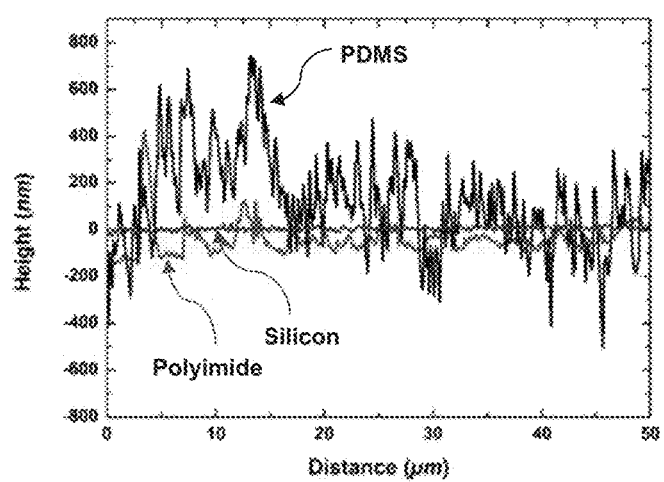
FIG. 4 shows a comparison of surface roughnesses of ZnO thin films sputter-deposited on: polyimide, transferred onto polydimethylsiloxane (PDMS), and silicon, as determined using surface profilometry.

FIG. 4 shows a comparison of the surface profiles of the oxygen-deficient ZnO thin films formed on: (a) polyimide, (b) PDMS, and (c) silicon along these segments. Table 1 shows the average surface roughness ($R_a$) of the ZnO thin film formed on each of the different substrates.

TABLE 1

Average surface roughness $R_a$ of ZnO on the different sensing substrates.

| Substrate | Average Surface Roughness $R_a$ (nm) |
|---|---|
| Silicon | 6.08 |
| Polyimide | 43.26 |
| PDMS | 160.29 |

It is clearly seen that the surface roughness is considerably higher on the elastomers (polyimide and PDMS), which concurs with the observation made using the SEM images. As such, the inventors believe that the increased surface area (owing to a higher surface roughness) on the elastomeric substrates leads to better sensing performance.

In the case of the In a similar fashion to the large area stretchable micro-tectonic ZnO-based sensor described above, the as-deposited oxygen-deficient ZnO thin film, the sputter-deposited oxygen-deficient ZnO thin film has an average surface roughness that falls within a range of about 40 nm to about-170 nm. X-ray diffraction (XRD) can be used to determine the crystallographic structure of the oxygen-deficient ZnO thin films formed on specific substrates.

Figure 5:
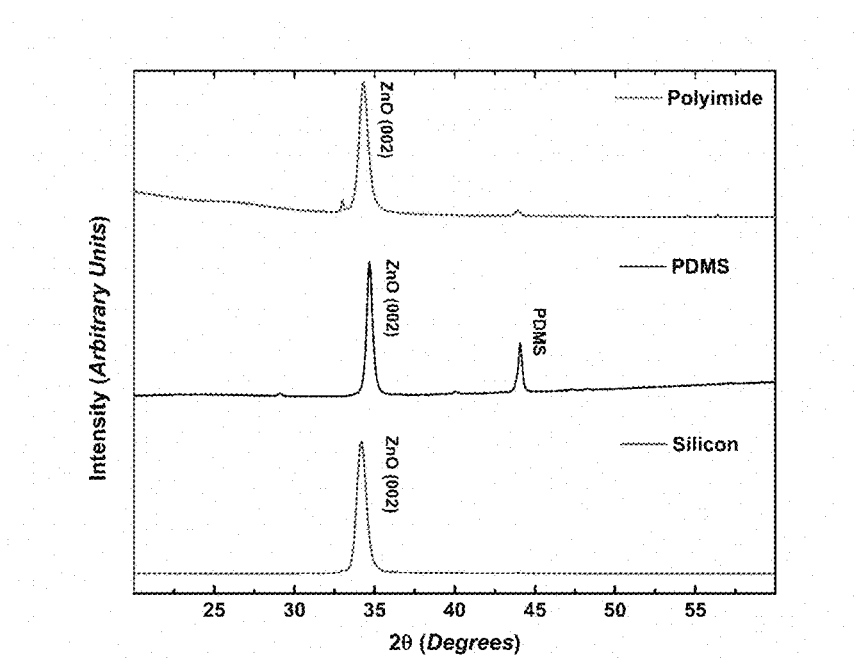
FIG. 5 shows a comparison of crystallographic structures of oxygen-deficient ZnO thin films sputter-deposited on polyimide, transferred onto polydimethylsiloxane (PDMS), and silicon, as determined using x-ray diffraction (XRD)

Referring to FIG. 5, there is shown a comparison of XRD diffractograms of oxygen-deficient ZnO thin films grown on polyimide, PDMS, and silicon. The ZnO thin films deposited on silicon and polyimide substrates show a strongly textured with a dominant (002) orientation. The ZnO thin film transferred to PDMS also show a strong (002) orientation, although no significant peak broadening and/or shift were observed for the transferred thin film on PDMS in comparison to the directly deposited films on silicon and polyimide. These results clearly illustrate that the crystal structure of the as-formed ZnO thin films is not altered by the transfer process or by deposition onto polyimide substrates.

The oxygen content in sputter-deposited ZnO thin films is controlled by altering the oxygen partial pressure during the sputtering process.[12,13] Thus, X-ray photoelectron spectroscopy (XPS) can be used to ensure that the sputtered ZnO thin films formed on substrates are oxygen-deficient and therefore able to exhibit the desired sensing capabilities. It is noteworthy, however, that neither of the two cited references[12,13] specifically relate to oxygen-deficient ZnO thin films formed on flexible or stretchable substrates.

Figure 6:
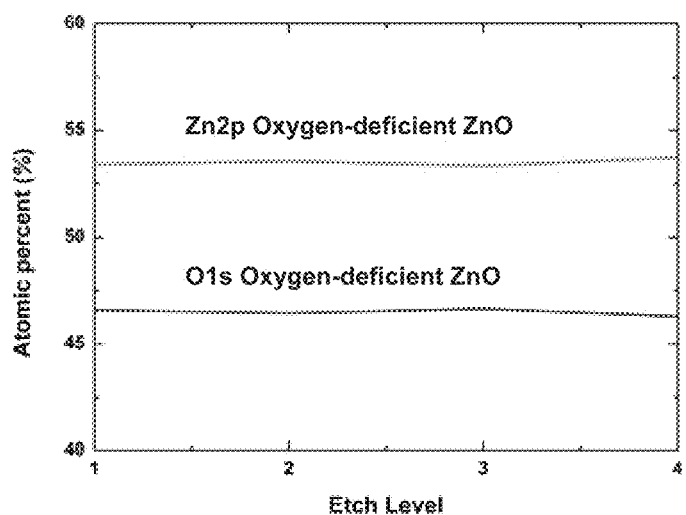
FIG. 6 shows a depth profile of extracted atomic concentrations of zinc and oxygen of an oxygen-deficient ZnO thin film sputter-deposited and transferred onto polydimethylsiloxane (PDMS), as determined by X-ray photoelectron spectroscopy (XPS)

FIG. 6 shows an XPS analysis of an oxygen-deficient ZnO thin film sputter-deposited on a substrate according to the method above. The results displayed clearly show that the oxygen deficient nature extends throughout the entire thickness of the sputter-deposited ZnO thin film.

Sensor Applications

In order to fully realize the stretchable oxygen-deficient ZnO-based sensor, according to the preferred embodiment of the present invention, the large area stretchable micro-tectonic ZnO-based sensor or the stretchable nano-patterned ZnO-based sensor produced according to the above method are modified to include pairs of terminal electrodes, which are disposed on the stretchable substrate in mutually spaced apart and opposing relation, and in electrical contact with the oxygen-deficient ZnO thin film acting as the sensing element of the oxygen-deficient ZnO-based sensor.

Sensing Capabilities

Specific embodiments that demonstrate the effectiveness of the stretchable oxygen-deficient ZnO-based sensors for detecting substances and/or electromagnetic radiation impinging thereon will now be described.

Substances

The sensing capability of the micro-tectonic oxygen-deficient ZnO-based sensor toward gaseous substances, in particular, hydrogen gas and nitrogen dioxide gas, has been tested and the results of the test are provided below.

It will be appreciated by those skilled in the relevant art however, that the choice of test substance is not simply limited to hydrogen gas and nitrogen dioxide gas, but may be expanded to include other gases such as, for example $SF_6$ and $C_4H_{10}$, and liquids such as, for example, gasoline and $C_2H_5OH$.

The oxygen-deficient nature of ZnO is reported to allow for higher adsorption of the test gases (hydrogen and nitrogen dioxide) which directly translates to superior sensitivity.[14,15] However, it is noteworthy that the two cited references[14,15] are clearly theoretical experiments, and neither reference relates to oxygen-deficient ZnO thin films formed on flexible or stretchable substrates.

The electrical resistance characteristics of the stretchable micro-tectonic oxygen-deficient ZnO-based sensor were acquired in situ under sequential exposure to zero air, hydrogen gas, and nitrogen dioxide gas. Such a sequence of exposure allows the study of the dynamic response of the stretchable micro-tectonic oxygen-deficient ZnO-based sensor towards a reducing and an oxidizing gas in a single exposure cycle. A rigid, smooth ZnO thin film on silicon was defined with identical electrodes and used as a comparative reference. Changes in ZnO resistance for the stretchable sensors was acquired in both relaxed and strained states, details of which are stated in the Experimental Details section below.

Figure 7:
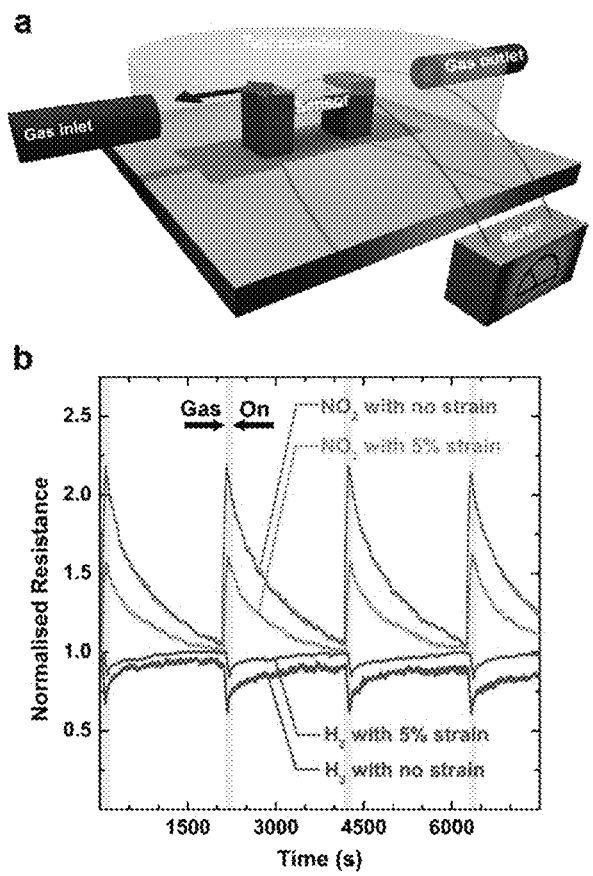
FIG. 7 shows (a) a schematic representation of a set up for detecting a gas using the micro-tectonic oxygen-deficient ZnO-based sensor (ZnO/PDMS) mounted within a chamber with controlled gas flow and in situ resistance measurement, and (b) a room temperature response of the stretchable micro-tectonic oxygen-deficient ZnO-based sensor (ZnO/PDMS) when exposed to hydrogen gas and nitrogen dioxide gas in relaxed (no strain) and stretched (5% strain) states (grey/shaded areas represent gas exposure for 80 s)

FIG. 7(a) shows a schematic representation of a typical set up for detecting a gas using the stretchable micro-tectonic oxygen-deficient ZnO-based sensor. The sensor is mounted on a platform within in a test chamber with a controlled gas flow and in situ resistance measurement (meter).

Briefly, the method of detecting a gas using the stretchable micro-tectonic oxygen-deficient ZnO-based gas sensor comprises the following steps of: (i) passing the gas over the oxygen-deficient ZnO-based sensing element so that the gas molecules contact the sensing element, (ii) applying a voltage across the stretchable micro-tectonic oxygen-deficient ZnO-based gas sensor, and (iii) using the meter to detect the electrical signal generated between the terminal electrodes that is proportional to a resistance value corresponding to a sensing of the substance impinging on the sensing element.

FIG. 7(b) shows a room temperature dynamic response of the stretchable micro-tectonic oxygen-deficient ZnO-based sensor when exposed to hydrogen gas and nitrogen dioxide gas in relaxed and stretched states (grey/shaded areas represent gas exposure for 80 s) when a manual force is applied to the stretchable micro-tectonic oxygen-deficient ZnO-based sensor during measurement. It will be appreciated that the force applied to the stretchable micro-tectonic oxygen-deficient ZnO-based sensor may be a stretching force, a compressive force, a twisting force, and a bending force. In some instances, it will be appreciated that the applied force may be a combination of forces such as for example, a combination of a stretching and a twisting force. It will be appreciated that when a force is applied to the stretchable micro-tectonic oxygen-deficient ZnO-based sensor, the oxygen-deficient ZnO sensing element is also caused to flex or stretch to a degree.

As shown in FIG. 7(b), the room temperature dynamic response of the stretchable micro-tectonic oxygen-deficient ZnO-based sensor shows a clear response to hydrogen gas. The exposure results in a rapid decrease in resistance and an inverted exponential recovery. The stretchable micro-tectonic oxygen-deficient ZnO-based sensor also shows a high converse sensitivity (resistance goes up on exposure) to nitrogen dioxide gas and a soft quadratic recovery. Under strain (up to 5%), a reduction in sensitivity is observed even though the response characteristic is maintained. The inventors have found that the stretchable micro-tectonic oxygen-deficient ZnO-based sensor shows high stability in its relaxed and strained states upon multiple exposures.

Based on the results shown in FIG. 7(b), it can be seen that both test gases (hydrogen and nitrogen dioxide) have opposite effects on the resistance, which can be utilized to clearly distinguish between the reducing (hydrogen) and oxidizing (nitrogen dioxide) gases. The mechanism of gas interaction with the sensing material is largely governed by the chemical properties of each material. Hydrogen is a reducing (electron-donating) gas, and hence, the resistance of the oxygen-deficient ZnO thin film decreases. On the other hand, a reaction with an oxidizing gas such as nitrogen dioxide would cause depletion of carriers from the valence band and cause an increase in the material's resistance. The inventors have pleasingly found that the novel category of micro-tectonic gas sensors exhibits a response that is comparable to other high sensitivity surface-enhanced gas sensors for hydrogen[16] and nitrogen dioxide.[17]

Whilst not wishing to be bound by any one particular theory, it is believed that the reduction in sensitivity seen on the application of strain can be attributed to the micro-tectonic nature of the sensor. The performance of the stretchable micro-tectonic oxygen-deficient ZnO-based sensor under stress is largely governed by the effective reduction of the active area of the oxygen-deficient ZnO thin film. With increasing strain, a smaller number of micro-tectonic plates stay in contact. This results in an overall reduction in the active area of the conductometric gas sensor, resulting in an increase in the baseline resistance ($R_0$) of ZnO. Therefore, no change in the response pattern is observed, other than a reduction in sensitivity. Furthermore, the inventors believe that the reduction in sensitivity is an indication that the overlapping ZnO micro-tectonic plates do not show a piezotronic effect owing to their morphology.[18-21] Such an effect was also observed and described by Gutruf et al.,[11] where the resistance of ITO micro-tectonic plates changed similarly under applied strain.

To effectively benchmark the gas sensitivity of the micro-tectonic surface of the oxygen-deficient ZnO thin film of the sensor, the inventors fabricated a rigid counterpart in which an oxygen-deficient ZnO thin film was sputter-deposited on a silicon wafer (ZnO/silicon) using identical fabrication parameters.

Figure 8:
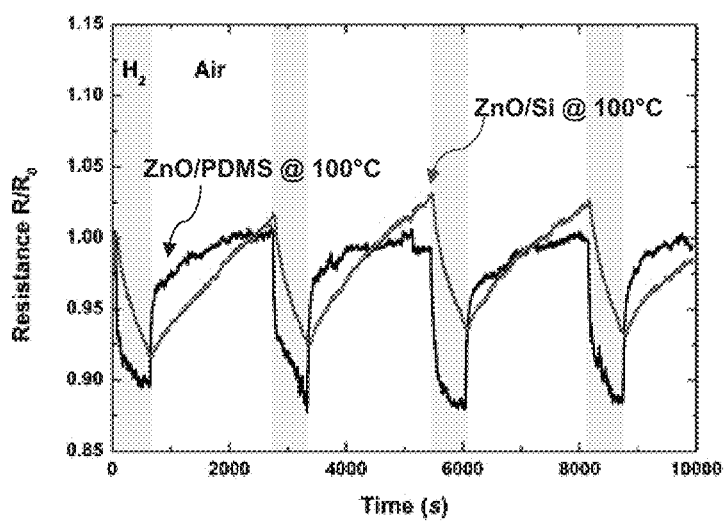
FIG. 8 shows the dynamic response of the stretchable micro-tectonic oxygen-deficient ZnO-based sensor (ZnO/PDMS) compared with that of a rigid counterpart (ZnO/silicon) when exposure to 1% hydrogen gas (200 sscm balanced in zero air) at a constant elevated temperature (100° C.)

FIG. 8 shows the dynamic response of the stretchable micro-tectonic oxygen-deficient ZnO-based sensor (ZnO/PDMS) compared with that of the rigid counterpart (ZnO/silicon) under cyclic exposure to hydrogen (200 sccm of 1% hydrogen balanced in zero air) for 10 min followed by 35 min recovery in zero air cycles. Both sensors were kept at a constant temperature of 100° C. throughout the measurements. The elevated temperature is essential for the optimum functionality of the rigid sensors.

Owing to the considerably lower sensitivity of the rigid counterpart, an elevation in operating temperature and a larger gas exposure time were required to obtain a measurable response from the rigid counterpart. As such, both the stretchable micro-tectonic oxygen-deficient ZnO-based sensor (ZnO/PDMS) and its rigid counterpart (ZnO/silicon) were tested under identical temperature and exposure conditions to ensure an accurate comparison. It is seen that the micro-tectonic sensor shows a higher sensitivity (>20%) and a significantly faster response than its rigid counterpart.

It is evident that the flexible micro-tectonic oxygen-deficient ZnO-based sensor (ZnO/PDMS) exhibits superior sensing speed, recovery and sensitivity compared to the rigid counterpart (ZnO/silicon) sensor. The superiority of the stretchable ZnO/PDMS sensor can be attributed to: (i) the highly gas permeable nature of PDMS especially towards hydrogen, and (ii) the unique micro-tectonic morphology of the ZnO thin film on PDMS. Both these factors result in an increased exposed surface area that reacts with the sensing gas.

Whilst not wishing to be bound by any one particular theory, it is believed that the increased sensitivity of the stretchable micro-tectonic oxygen-deficient ZnO-based sensor (ZnO/PDMS) compared to the rigid counterpart (ZnO/silicon) is caused by multiple factors. Firstly, an enhanced surface area due to the micro-tectonic morphology (FIG. 3 and FIG. 4) enables larger number of gas molecules to interact with the ZnO surface. Secondly, the gas permeable nature of PDMS towards both test gases further maximize the exposed area by allowing the diffusion of gas molecules through the bottom of the gas-permeable PDMS elastomeric substrate.

It is also evident that the stretchable micro-tectonic oxygen-deficient ZnO-based sensor (ZnO/PDMS) is capable of detecting hydrogen gas and nitrogen dioxide gas at temperatures that fall within a range consistent with the operational temperature range of the micro-tectonic oxygen-deficient ZnO-based sensor (ZnO/PDMS), that is, 20 degrees Centigrade to 50 degrees Centigrade. This clearly distinguished the as-fabricated stretchable oxygen-deficient ZnO-based gas sensor from its rigid counterpart in that the gas detection can even occur at room temperature.

The inventors believe that this transparent, lightweight, stretchable and highly sensitive stretchable micro-tectonic oxygen-deficient ZnO-based sensor is highly relevant for portable hazardous gas detection, due to its low energy consumption, robustness, and curvilinear adaptability.

Reversible Ultra-Violet Photosensitivity

The sensing capability of the stretchable micro-tectonic oxygen-deficient ZnO-based sensor toward electromagnetic radiation, more particularly ultra-violet (UV) radiation, has been tested and the results of the test are provided below.

Figure 9:
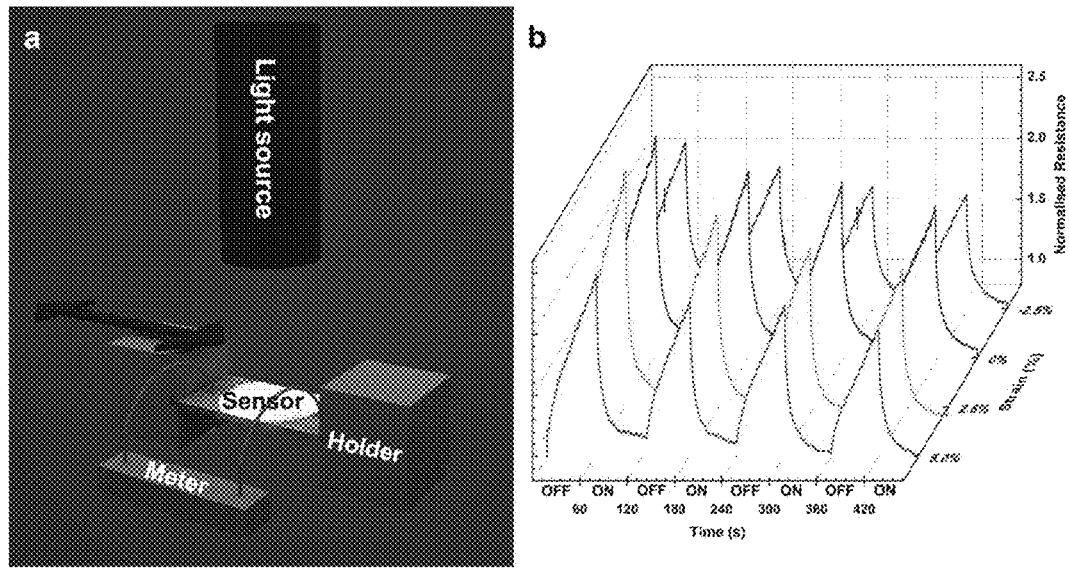
FIG. 9 shows (a) a schematic representation of a set up for detecting ultra-violet (UV) radiation using the stretchable micro-tectonic oxygen-deficient ZnO-based sensor (ZnO/PDMS) with resistance measurement, and (b) normalized resistance under cyclic exposure to darkness (OFF state) and broadband UV illumination of 1 sun (ON state) for different levels of uniaxial strain (from −2.5% compression to 5% strain)

FIG. 9(a) shows a schematic representation of a set up for detecting ultra-violet (UV) radiation emitted from a high energy UV illumination source with the stretchable micro-tectonic oxygen-deficient ZnO-based UV sensor under an applied force (elongation and compression) using a high resolution micro-scale stretching apparatus with in-situ resistance measurement.

Briefly, the method of detecting ultra-violet (UV) radiation using the stretchable micro-tectonic oxygen-deficient ZnO-based UV sensor comprises the following steps of: (i) illuminating the oxygen-deficient ZnO-based sensing element with ultra-violet (UV) radiation emitted from the high energy UV illumination source so that the radiation contacts or impinges on the sensing element, (ii) applying a voltage across the stretchable micro-tectonic oxygen-deficient ZnO-based UV sensor, and (iii) using the meter to detect the electrical signal generated between the terminal electrodes that is proportional to a resistance value corresponding to a sensing of the ultra-violet (UV) radiation impinging on the sensing element.

FIG. 9(b) shows the dynamic response of resistance of the stretchable micro-tectonic oxygen-deficient ZnO-based sensor subject to cyclic exposure to darkness (OFF state) and broadband UV illumination of 1 sun (ON state) for different levels of uniaxial strain. Upon exposure to UV light, the resistance of the flexible micro-tectonic oxygen-deficient ZnO-based sensor decreases. The device state under UV exposure is termed hereinafter as ON, while the ambient light state is termed hereinafter as OFF.

The resistance of the stretchable micro-tectonic oxygen-deficient ZnO-based sensor in the OFF state is dependent on the intensity of ambient light and can result in an open circuit measurement in absolute darkness. On the other hand, the ON state is highly stable, and is therefore used as the steady state. As such, all the resistance values were normalized to the ON state resistance. This normalisation is necessary to ensure an accurate comparison between the sensors at varying strain states owing to their different initial resistance values.

The stretchable micro-tectonic oxygen-deficient ZnO-based sensor was tested both in a relaxed as well as mechanically strained state. In a relaxed state (no strain) and given a limited recovery time of 60 s an average OFF/ON ratio of 2.25 is consistently observed. To further assess the sensor performance, a larger recovery period of 900 s was allowed.

FIG. 9(b) shows that under compression and strain of up to 2.5%, little variation in the performance of the stretchable micro-tectonic oxygen-deficient ZnO-based sensor is seen. On being stretched beyond 2.5% strain under compression, a slight decrease in the OFF/ON ratios can be observed.

Whilst not wishing to be bound by any one particular theory, it is believed that this can be ascribed to the disconnection of some ZnO micro-tectonic plates on being forced apart due to the applied strain. This creates a gradual build-up of non-conductive areas, causing an increase in resistance, to a point where the film eventually becomes insulating, leading to an open circuit measurement.[11] Effectively, this leads to a reduction in the active sensing area of the oxygen-deficient ZnO thin film (the sensing element) which explains the drop in performance once stretched. Similarly, the stretchable micro-tectonic oxygen-deficient ZnO-based sensor also showed a slightly deteriorated response under compression, which can be attributed to a decrease in exposed surface area, as well as bowing of the underlying PDMS substrate, and as a result, the ZnO plates also. The nearly linear recovery along with a cubic response to UV light is comparable to nanoparticle[22] or nanowire[23] based sensors reported elsewhere, which suggests that the sensor performance of the stretchable micro-tectonic oxygen-deficient ZnO-based sensor is largely governed by the surface morphology.

Importantly, when compared to strained nanowire ZnO sensors, it becomes evident that a better performance under strain can be achieved with the stretchable micro-tectonic oxygen-deficient ZnO-based sensor.[24]

To effectively benchmark the performance of the stretchable micro-tectonic oxygen-deficient ZnO-based sensor (ZnO/PDMS), the inventors fabricated a flexible analog in which an oxygen-deficient ZnO thin film was sputter-deposited on polyimide substrate (ZnO/polyimide) and a rigid counterpart in which an oxygen-deficient ZnO thin film was sputter-deposited on a silicon wafer (ZnO/silicon) using identical fabrication parameters.

Figure 10:
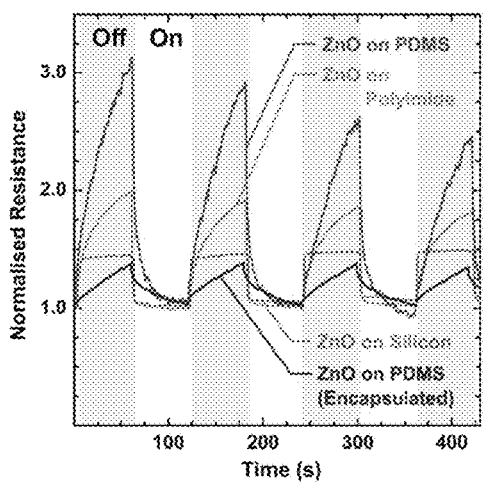
FIG. 10 shows a normalised change in resistance response to determine UV sensitivity of oxygen-deficient ZnO thin films sputter-deposited on silicon, polyimide, transferred onto polydimethylsiloxane (PDMS) and polydimethylsiloxane (PDMS, encapsulated), (shaded area represents the OFF state for 60 s, and light area represents the ON state for 60 s)

FIG. 10 shows a comparison of the UV sensitivity of the stretchable micro-tectonic oxygen-deficient ZnO-based sensor (ZnO/PDMS) against those of the flexible analog (ZnO/Polyimide) and the rigid counterpart (ZnO/silicon).

Whilst not wishing to be bound by any one particular theory, it is believed that the high sensitivity of the stretchable micro-tectonic ZnO thin film sensors relies on the following mechanism that drives a reversible change in resistance. The oxygen-deficient nature of the ZnO thin films used in this study attracts ambient oxygen, resulting in its adsorption on to the ZnO thin film surface. The electrical conduction decreases when oxygen is absorbed from ambient air, resulting in the formation of a depletion layer on the ZnO surface (OFF state). When exposed to UV light, the photogenerated carriers driven by the resulting electric field move to the surface, where they neutralize the absorbed oxygen leaving behind unpaired electrons which result in the increased conductivity (ON state).[23] It is also believed that the aforementioned process is further facilitated by the micro-tectonic morphology of the ZnO thin film, which provides a larger surface area for the oxygen adsorption, and hence, a greater proportion of unpaired carriers. This effect results in the enhanced OFF/ON ratios seen in the stretchable micro-tectonic oxygen-deficient ZnO-based sensor (ZnO/PDMS).

As shown in FIG. 10, the performance of the flexible analog (ZnO/polyimide) shows an inverted cubic recovery with a sharp response to UV exposure, albeit with a lower sensitivity compared to the stretchable micro-tectonic oxygen-deficient ZnO-based sensor (ZnO/PDMS). The inventors believe this clearly indicates that a rough surface provides more surface area for oxygen adsorption, and therefore, the change in resistance is higher on UV exposure. The effect of surface roughness on the sensing performance is clearly highlighted in FIG. 5 and in the results given in Table 1, where it is observed that a higher surface roughness results in a greater sensitivity. As such, the stretchable micro-tectonic oxygen-deficient ZnO-based sensor (ZnO/PDMS) outperforms the flexible analog (ZnO/polyimide) and the rigid counterpart (ZnO/silicon).

This hypothesis is further tested by encapsulating the stretchable micro-tectonic oxygen-deficient ZnO-based sensor (ZnO/PDMS) to minimize the rate of oxygen adsorption on the ZnO thin film surface. As expected, and as shown in FIG. 10, the sensitivity drops significantly.

Figure 11:
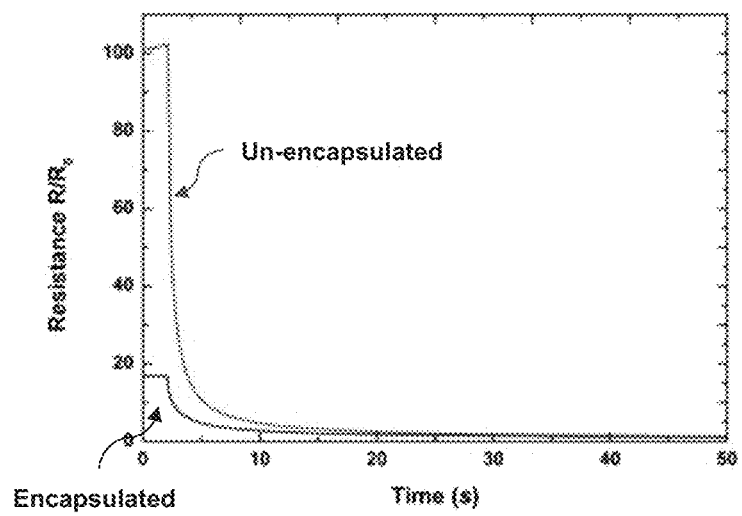
FIG. 11 shows a normalised change in resistance response of oxygen-deficient ZnO thin films sputter-deposited and transferred onto polydimethylsiloxane (PDMS) (encapsulated and un-encapsulated) when exposed to ultra-violet (UV) radiation (48 s) after a preceding long recovery period (15 min)

FIG. 11 shows the normalized change in resistance of the sensor response times for the encapsulated and un-encapsulated stretchable micro-tectonic oxygen-deficient ZnO-based (ZnO/PDMS) sensors when exposed to ultra-violet (UV) radiation (48 s) after a preceding long recovery period (15 min). OFF/ON ratios of 100 for the un-encapsulated (ZnO/PDMS) sensor and 18 for the encapsulated (ZnO/PDMS) sensor were observed. The increased ON/OFF ratio of the sensors is due to a longer recovery time, which leads to a higher adsorption of oxygen, resulting in a larger resistance. In case of the encapsulated (ZnO/PDMS) sensor, the adsorption is slowed down by the PDMS which results in a relatively smaller increase in resistance.

The results show that when given sufficient recovery time, the encapsulated (ZnO/PDMS) sensor still shows an OFF/ON ratio of 16 which is due to the oxygen permeable nature of PDMS which allows the ambient oxygen to gradually diffuse.

In order to compare the performance of oxygen-deficient ZnO thin films on substrates of increasing surface roughness, the response speed of the rigid counterpart (ZnO/silicon), the flexible analog (ZnO/polyimide) and a confirmed micro-tectonic ZNO thin film formed on Si (Micro-tectonic ZnO on Si) were subject to broadband radiation. The ON and OFF speed was measured with respect to the rigid counterpart (ZnO/silicon), which is the sensor with the lowest sensitivity. The sensors were considered ON and OFF when reaching a resistance change (R/R$_0$) of 0.4.

TABLE 2

Comparison of ON and OFF speeds for UV photosensitivity

| Substrate | OFF Speed (s) | ON Speed (s) |
|---|---|---|
| ZnO on Silicon | 3.5 | 3.0 |
| ZnO on polyimide | 9.0 | 2.0 |
| Micro-tectonic ZnO on Si | 7.0 | 1.5 |

It can be seen from FIG. 10 and from the results in Table 2, that the OFF speed of the sensors with a ZnO thin film formed on polymeric substrates is slower than their rigid counterpart (ZnO/silicon), while the ON speed outperforms the rigid sensors consistently.

Temperature Dependent Photosensitivity Measurements

In order to eliminate the possibility of the crystal structure alterations affecting the behaviour of the micro-tectonic ZnO thin film, a temperature dependent photosensitivity measurement was carried out using the stretchable micro-tectonic oxygen-deficient ZnO-based sensor (ZnO/PDMS). The inventors consider that this is important to confirm that the increase in sensitivity of ZnO thin films formed on elastomeric based platforms in comparison to ZnO thin films formed on rigid substrates is largely governed by the surface topography.

The stretchable micro-tectonic oxygen-deficient ZnO-based sensor (ZnO/PDMS) was placed on a temperature controlled stage (Linkam HFS600E-P with a Linkam T95-PE controller) and was then subjected to UV light with a 1 min exposure followed by 1 min darkness. Measurements were taken at room temperature, 100° C., and 150° C.

Whilst not wishing to be bound by any one particular theory, it is believed that elevated temperatures induce a thermal expansion mismatch between the oxide thin film and PDMS stressing the ZnO thin film, thereby causing a change in crystal structure.[25]

Figure 12:
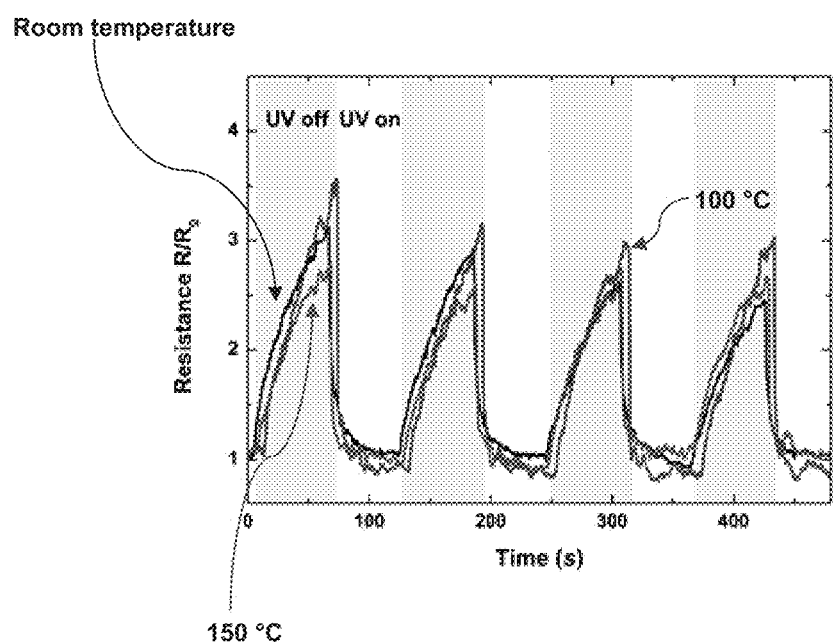
FIG. 12 shows a normalised change in resistance response of an oxygen-deficient ZnO thin film sputter-deposited and transferred onto polydimethylsiloxane (PDMS) when exposed to ultra-violet (UV) radiation at room temperature, 100° C. and 150° C., (shaded area represents the OFF state for 60 s, and light area represents the ON state for 60 s))

The results of the study shown in FIG. 12 reveal only a slight variation in sensitivity and no change in the response parameters. Whilst not wishing to be bound by any one particular theory, it is believed that this is mainly because the micro-tectonic ZnO plates of the ZnO thin film slide over each other under strain, thereby preventing a thermal stress induced band shift. It is therefore apparent that the higher sensitivity of the stretchable micro-tectonic oxygen-deficient ZnO-based sensor (ZnO/PDMS) is largely attributed to the unique high roughness surface structure.

By virtue of these results, it is clear that the stretchable micro-tectonic oxygen-deficient ZnO-based sensor (ZnO/PDMS) exhibits excellent thermal stability and, as such, is capable of detecting ultra-violet (UV) radiation at a temperature that falls within the operational range of the stretchable micro-tectonic oxygen-deficient ZnO-based sensor (ZnO/PDMS) itself, that being between generally 20 degrees Centigrade and 50 degrees Centigrade.

UV Transmission Measurement

The inventors also conducted transmission measurements to ascertain the spectral sensitivity of the stretchable micro-tectonic oxygen-deficient ZnO-based sensor (ZnO/PDMS).

Thus, to determine the absorption wavelength range of the oxygen-deficient ZnO thin film and therefore the spectral sensitivity of the sensor, a transmission measurement was performed. The measurement was taken using a Craic PV20/30 micro-photo spectrometer with an uncoated PDMS as reference.

Figure 13:
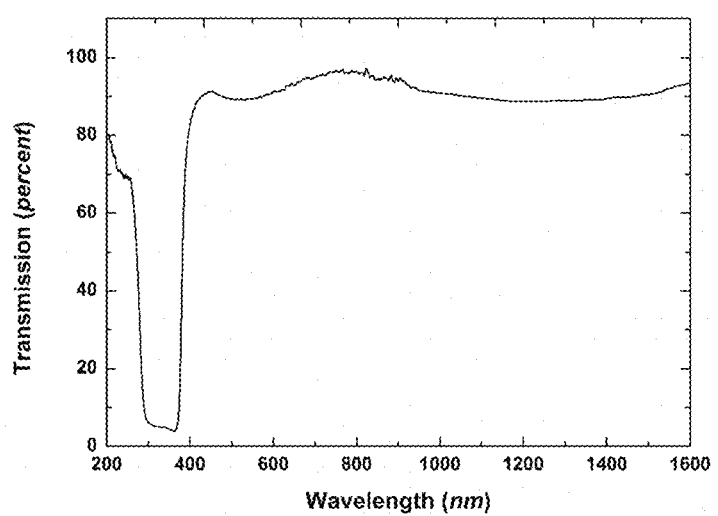
FIG. 13 shows the transmission characteristics of an oxygen-deficient ZnO thin film sputter-deposited and transferred onto polydimethylsiloxane (PDMS) for use in determining the spectral sensitivity of the flexible micro-tectonic oxygen-deficient ZnO-based sensor (ZnO/PDMS)

FIG. 13 shows a broad absorption between 200 nm and 420 nm, with a particular clear absorption wavelength range between 280 nm to 400 nm, benchmarking the spectral sensitivity of the stretchable micro-tectonic oxygen-deficient ZnO-based sensor (ZnO/PDMS). This implies that the ZnO-based micro-tectonic sensor is clearly UV sensitive within the wavelength range of 280 to 400 nm. This finding indicates that the sensitivity of the stretchable micro-tectonic oxygen-deficient ZnO-based sensor (ZnO/PDMS) lies directly in the UV-A (400 nm-320 nm) and UV-B bands (320-280 nm).[26]

By virtue of this finding, there is a reasonable argument to suggest that the stretchable micro-tectonic oxygen-deficient ZnO-based sensor (ZnO/PDMS) can be harnessed to detect the most harmful type of UV light and can prove crucial for the prevention of skin aging, eye damage, and skin cancer by offering enhancement in the active and responsive functional oxide area. It will be appreciated by persons of ordinary skill in the art that by, for example, modifying the surface of the oxygen-deficient ZnO thin film or by simply substituting the oxygen-deficient ZnO thin film for another metal oxide, it will be possible to tune the range of wavelengths of electromagnetic radiation to be detected accordingly.

Mechanically Tunable Diffraction Gratings

The ability to realize sub-micron ZnO structures on a stretchable PDMS substrate provides an opportunity to exploit their characteristics in the optical domain as well. One class of optical components often requiring sub-micron features are diffraction gratings which are already found in a wide of range of applications in telecommunications[27] and spectroscopy.[28] The use of a stretchable substrate, such as PDMS, offers the potential for tuning the grating's period and diffraction properties via mechanical deformation.[29]

The novel fabrication technique for producing such micro-tectonic oxygen-deficient metal oxide thin films allows the realization of tunable diffraction gratings that can be periodic in both dimensions and incorporate metal oxides like ZnO or $TiO_2$.

The following describes the fabrication of ZnO/PDMS diffraction gratings to demonstrate surface strain sensing with a high degree of accuracy without considerable mechanical impact on the underlying elastomeric substrate.

ZnO was deposited onto an electron beam lithographically defined structure, and patterned by a 'lift-off' process. The device comprised of a ~2 mm thick PDMS substrate with an embedded ZnO grating with a short grating period of 1 μm and an overall size of 125 $μm^2$. A ZnO film thickness of 70 nm was used to introduce the minimum possible high modulus material to minimize mechanical impact on the substrate.

Figure 14:
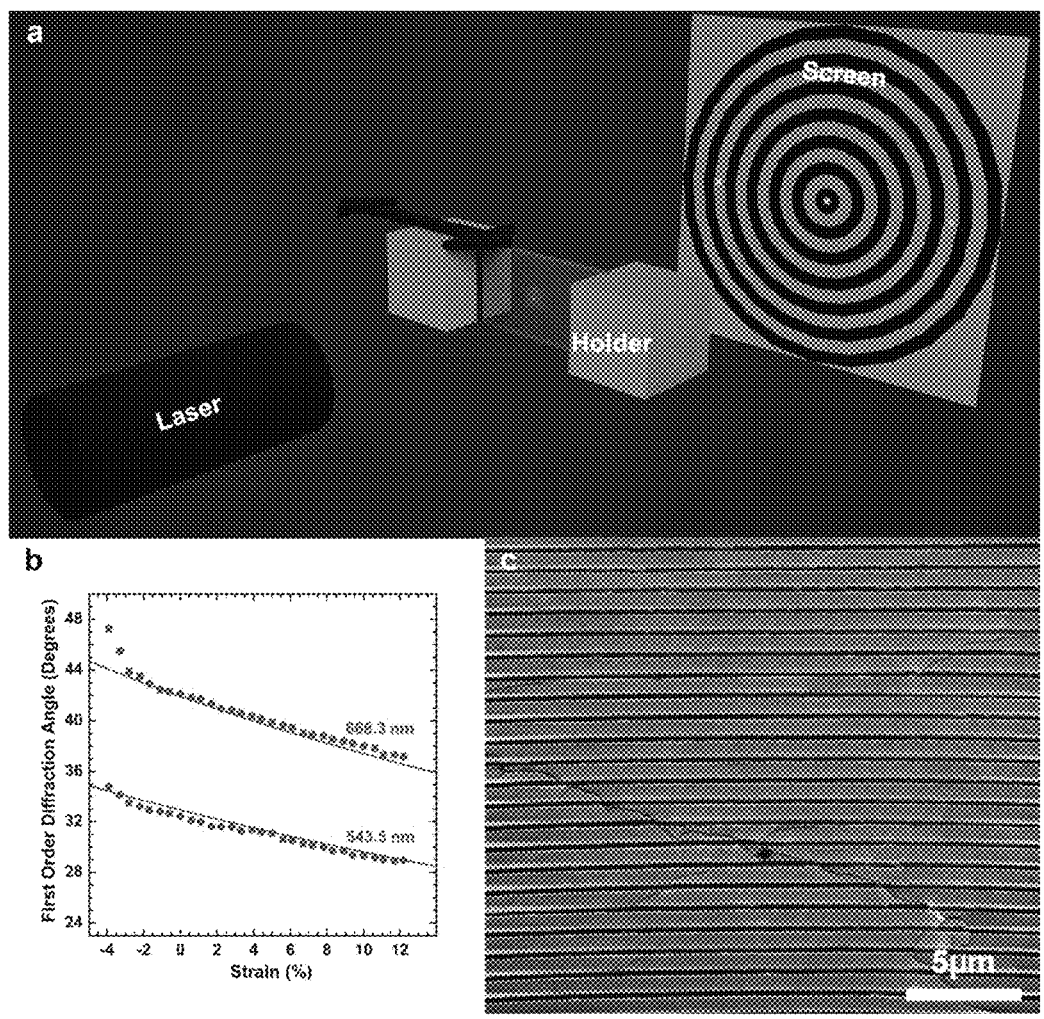
FIG. 14 shows (a) a schematic representation of a set up comprising a laser, a high-resolution stretching stage for mounting a stretchable oxygen-deficient ZnO thin film (nano-patterned with a diffraction grating) embedded in polydimethylsiloxane (PDMS), and a screen located at a fixed length away from the ZnO thin film diffraction grating for visualizing a change in first order diffraction angle when the ZnO thin film diffraction grating is subject to a mechanical strain (ranging from −4% to 12%), (b) observed changes in first order diffraction angle with mechanical strain at two laser wavelengths (668.3 nm and 543.5 nm), and (c) an electron micrograph of the ZnO thin film diffraction grating after extensive testing.

FIG. 14(a) shows a schematic representation of an experimental setup composed of a high resolution stretching stage in which the device is clamped to allow for precise deformation. A laser is aimed at the gratings of a ZnO-based sensor which casts a first order diffraction pattern onto a semi-transparent back screen positioned at a fixed length away with calibrated marks for an accurate diffraction angle measurement.

Figure 15:
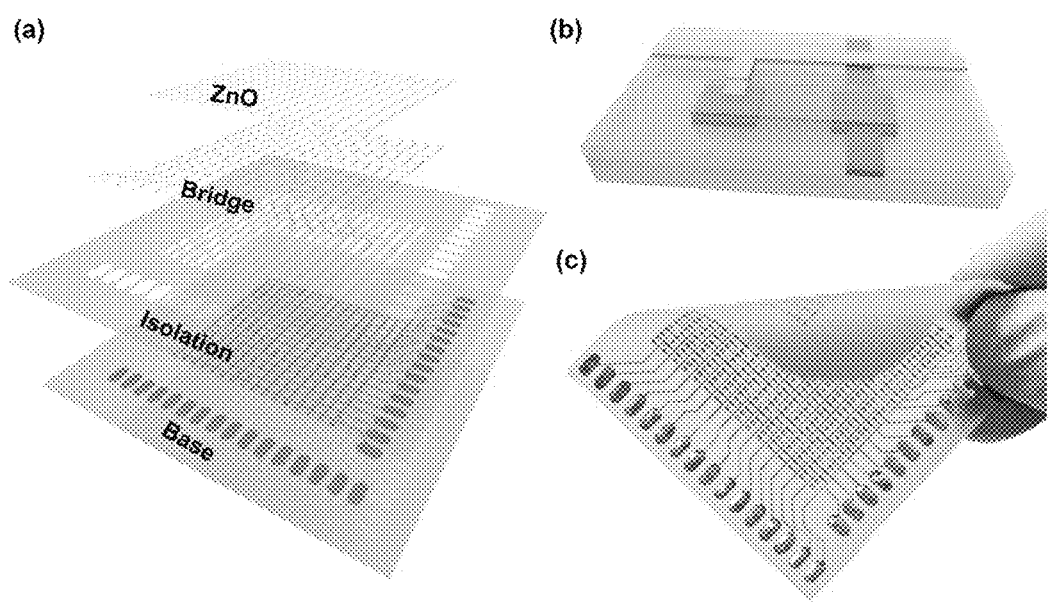
FIG. 15 shows schematic representations of (a) a flexible oxygen-deficient ZnO-based imaging array sensor (in exploded view) in accordance with another preferred embodiment of the present invention, (b) a magnified view of a single pixel of the flexible oxygen-deficient ZnO-based imaging array sensor, and (c) a photograph of the flexible oxygen-deficient ZnO-based imaging sensor with tinned ports ready for operation.
Figure 16:
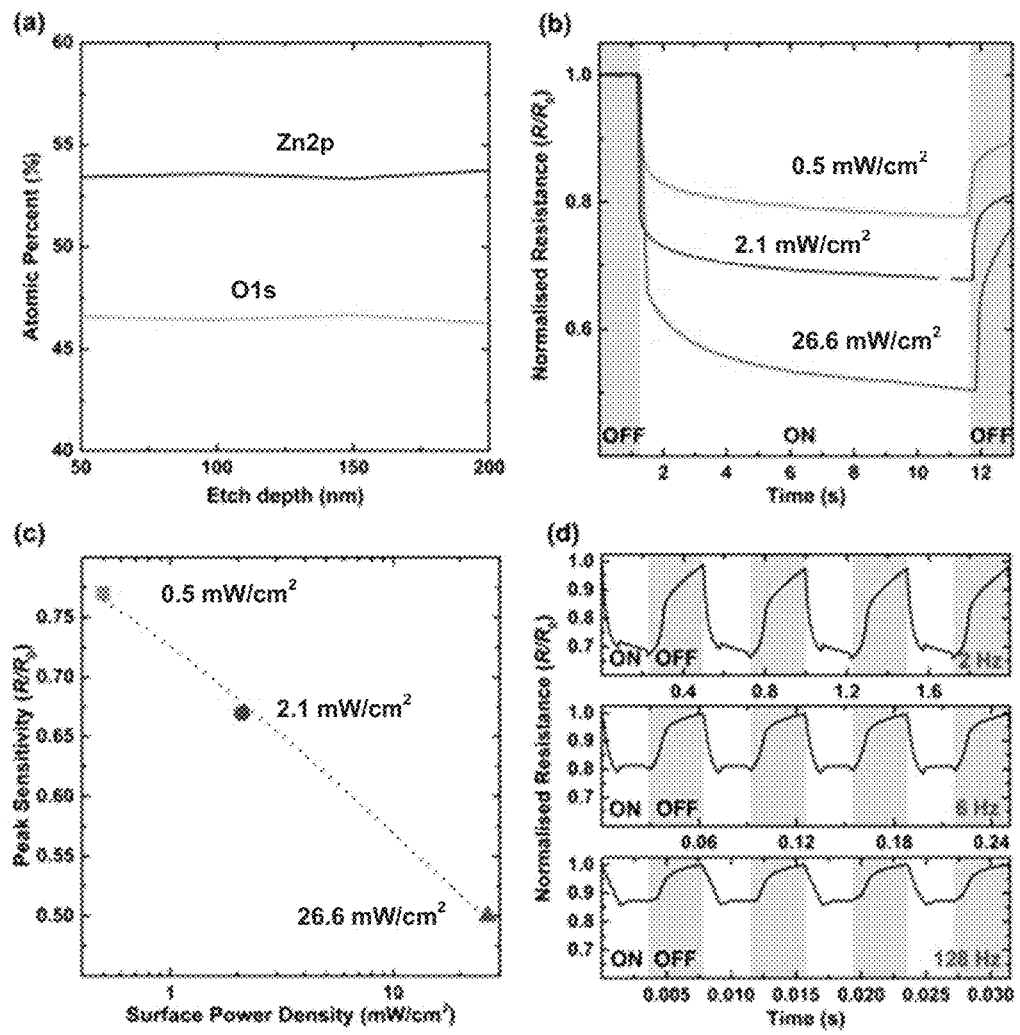
FIG. 16 shows (a) an X-ray photoelectron spectroscopy (XPS) depth profile of extracted atomic concentrations of zinc and oxygen of the oxygen-deficient ZnO thin film of the imaging array sensor of FIG. 15, (b) a normalised change in resistance response of a single pixel of the imaging array sensor of FIG. 15 when exposed to an ultra-violet (UV) wavelength of 365 nm for 10 s (normalized to the OFF state (shaded area) with logarithmically increasing UV intensity, 0.5 mW/cm$^2$, 2.1 mW/cm$^2$ and 26.6 mW/cm$^2$), (c) a plot of peak sensitivity ($R/R_0$) vs. incident UV power extracted (mW/cm$^2$) of data extracted from FIG. 16(b), shown with a logarithmically fitted trend line, and (d) a response to 25 mW/cm$^2$ at an ultra-violet (UV) wavelength of 365 nm with increasing frequency (2 Hz, 6 Hz and 128 Hz), (shaded area represents the OFF state)

FIG. 15 shows a spectrum of the red diode laser and the green He—Ne laser, while FIG. 16 shows an image of the back of the semi-transparent screen used to determine the distance from the zero order centerpoint.

The measurement was executed by applying negative and positive strain ranging from −4% to 12%, while the diffraction angle was observed in situ.

FIG. 14(b) shows the observed changes in first order diffraction angle with mechanical strain at two laser wavelengths. The data markers in FIG. 14(b) display the recorded diffraction angles for green and red laser illumination. The measured diffraction angles are in excellent agreement with the prediction based on the grating equation (1), presented in the Experimental Details section below. When the sample is compressed, the measured angles slightly deviate from the model, in particular for red light. This deviation is related to the bending of the PDMS film under compression, with the non-planar structure not considered by the analytical expression.

To evaluate the device performance and mechanical robustness after rough handling the grating was tested after being rotated by 90° so that the strain impacts perpendicular to the grating period and a strain of −4% to 12% was applied. As expected, only a slight change in diffraction angle (θ) was observed, which is caused by the intrinsic Poisson's ratio of PDMS (~0.5).

FIG. 14(c) shows a scanning electron micrograph of the fabricated ZnO diffraction gratings of the ZnO-based sensor after extensive stretching in the direction of the grating period and perpendicular to it. Apart from some minor cracks, the gratings structure remained largely intact, due to the strong adhesion to the PDMS substrate. The gratings remain fully functional even after the small cracks occur due to the oxide being embedded in the PDMS. Therefore, the significant refractive index contrast (PDMS~1.4, ZnO~2.0) is still intact resulting in no degradation of device performance.

Considering a possible detection of 0.1° change of the diffraction angle, in this simple measurement setup, the measurable change in strain is in the order of 0.26% and 0.36% for green light and 0.18% to 0.26% for red light over a strain range of −2% to 12%. In absolute terms, this equals to a change in period of 2.1 nm to 4.0 nm for green light and 1.8 nm to 2.9 nm for red light. In the tested device, the stretchable area is limited to 125 grating periods, allowing the measurement of absolute strain of ~300 nm using the green laser and ~250 nm when using the red laser.

The results show that the performance of the stretchable micro-tectonic oxygen-deficient ZnO-based sensor (ZnO/PDMS) agrees well with the calculated results and allows for surface strain measurement in the nanometer regime with little impact on the elastomeric substrate.

CONCLUSIONS

In conclusion, the inventors have demonstrated stretchable ZnO-based gas, UV, and strain sensing on a stretchable PDMS substrate, where the functional material, that is the oxygen-deficient ZnO sensing element, is stretchable itself.

It has also been shown that the as-produced stretchable sensor outperforms its more rigid counterparts (on silicon) and does not require elevated temperatures for efficient performance. In fact, the unique micro-tectonic structure of the functional oxygen-deficient ZnO thin film has been shown to result in enhanced sensing performance of the stretchable templates.

Experimental Section—Stretchable Sensor
Device Fabrication

The fabrication of the transparent PDMS-based ZnO devices relies on the platinum transfer technique described in detail in Gutruf et al.[11] The simplified production process is depicted in FIG. 1. The process starts with a platinum layer deposited by electron beam evaporation on a standard cleaned silicon wafer (FIG. 1a). Subsequently, 500 nm ZnO thin films with a preferential (002) crystal orientation were deposited on Pt/Si substrates from a pure zinc (99.99%) target via reactive DC magnetron sputtering at a temperature of 250° C. Detailed sputtering conditions are presented in Table 3.

ZnO Thin Film DC Sputtering Conditions

An oxygen ratio of 40% in the process gas results in crystalline ZnO thin films with almost stoichiometric elemental concentrations through their thickness. At an oxygen ratio of 15%, the O/Zn ratio drops to ~46% yielding oxygen deficient ZnO films. While stoichiometric ZnO films show an almost fully insulating behaviour, the conductivity of the ZnO films increases with decreasing the oxygen partial pressure. This can be ascribed to the presence of oxygen vacancies which act as n-type dopants in the ZnO lattice.[30-32]

The key sputtering parameters are summarised in Table 3.

TABLE 3

Sputtering conditions for ZnO thin films

| Substrate | Pt/Si |
|---|---|
| Target | Zn |
| Process Gas | 15% oxygen in argon |
| Base pressure | $1 \times 10^{-7}$ Torr |
| Sputtering Pressure | $5 \times 10^{-3}$ Torr |
| Substrate Temperature | 250° C. |
| DC Power | 200 W |
| Sputtering Rate | 8.5 nm/min |

The oxygen content in sputtered ZnO thin films is controlled by altering the oxygen partial pressure during the sputtering process.[12,13] N-type conduction behaviour of the films was verified with the hot point probe method.[33] Furthermore, the crystallinity of the sputter-deposited oxygen-deficient ZnO thin film was verified by XRD analysis (FIG. 5). The oxygen-deficient nature of the sputter-deposited oxygen-deficient ZnO thin film was verified by XPS analysis (FIG. 6).

The ZnO/Pt sandwich was then removed from its rigid carrier by casting PDMS (2 mm) onto the ZnO layer with a subsequent hot plate cure at 120° C. for 8 min and an immediate peel-off (FIG. 1c). The wafer-sized ZnO/PDMS device was flipped over onto a silicon carrier and the Pt layer was then removed by reactive ion etching (7.5 min, 100 W in argon atmosphere at 70 mTorr working pressure) leaving the ZnO exposed (FIG. 1d). The devices for the gas sensing and photosensitivity test were then carefully diced into 10 mm×20 mm specimens.

The fabrication of the nanoscale gratings occurs similar to the fabrication of the unpatterned devices, except for the additional lithography process. A 250 nm thick polymethyl methacrylate (PMMA) layer is applied to the platinum-coated silicon wafer via spin coating followed by a hard bake at 180° C. The electron beam sensitive PMMA is then exposed with an electron beam lithography system (Nabity EBL system on a FEI Nova SEM equipped with a field emission gun) writing the negative mask of the diffraction grating in a serial process. With a subsequent immersion in a MIBK developer to wash away the exposed regions of the transmission diffraction grating, the sample is then placed in the reactive sputterer to deposit 70 nm thick ZnO films at room temperature, in a 6:4 gas ratio of Ar/$O_2$ (FIG. 1f). Lift-off is then performed in an acetone bath removing the excess ZnO. Subsequently the finished gratings were heated to 400° C. for 1 h under oxygen atmosphere to render them transparent (FIG. 1g). Analogous to the non-patterned ZnO device production, PDMS was cast and cured on the gratings and then removed by peeling (FIG. 1h). Again, the platinum layer was removed by reactive ion etching (FIG. 1i) exposing the ZnO diffraction pattern. The devices where then removed from the carrier and diced into 30 mm×50 mm pieces.

Gas Sensitivity Testing

Gas sensitivity testing was conducted in a temperature controlled chamber (Linkam HFS600E-P with Linkam T95-PE controller) with gas flow control (MKS Multigas Controller 647B) (FIG. 3(a)). The stretchable oxygen-deficient ZnO-based gas sensor was mounted on the temperature controlled chuck and heated to 100° C. The resistance was measured in situ via copper pads of 0.5 $cm^2$ in area, placed carefully at a distance of 10 mm on the ZnO surface, held down by micro probes for both rigid ZnO and micro-tectonic surfaces. The room temperature measurements were conducted in a similar manner. The exposure of hydrogen (1% $H_2$ in zero air balance with a flow rate of 200 sccm) was followed by an exposure to zero air with a flow rate of 800 sccm to monitor the response speed of the sensor. The results demonstrate that the stretchable oxygen-deficient ZnO-based gas sensor is capable of detecting hydrogen gas concentrations down to a sensitivity of less than 1% $H_2$ in an air balance with a flow rate of 200 sccm.

The $NO_2$ testing was executed in a similar manner to the hydrogen sensing tests with $NO_2$ exposure (9.9 ppm of $NO_2$ in zero air balance) with a flow rate of 200 sccm, followed by a flow rate of 800 sccm of zero air.

The room temperature measurements were taken with a zero air exposure of 35 min and a subsequent 80 s exposure to hydrogen gas and nitrogen dioxide gas, respectively. The resistance measurements at elevated temperature were then acquired every second (FIG. 8) with an exposure of 35 min zero air and a subsequent 10 min hydrogen exposure. All gas sensing measurements were taken under a steady ambient illumination. The results demonstrate that the stretchable oxygen-deficient ZnO-based gas sensor is capable of detecting nitrogen dioxide gas concentrations down to a sensitivity of less than 9.9 parts per million in zero air at a flow rate of 200 sccm.

Photosensitivity Testing

Photosensitivity testing was conducted with a broadband light source (Abet Technologies Model LS150) as shown in FIG. 4a, and the shutter was operated manually in a 1 min dark/exposure cycle. The ZnO sensor was clamped on to a custom-made stretching stage with a displacement resolution of 2.5 µm. Subsequently, testing was conducted (FIG. 4(d)) under compression and elongation while monitoring the resistance in situ via bonded electrodes using gold ribbon and silver bonding epoxy.

Diffraction Angle Measurement

The angle of the diffracted light was predicted based on the grating equation for normal incidence according to equation (1):

$$\sin(\theta) = \frac{m\lambda}{\Lambda} \qquad \text{(Equation 1)}$$

where θ is the diffracted angle, m the diffraction order, λ the operating wavelength, and Λ the period of the diffraction grating.

The period of the diffraction grating was designed to be 1 μm in order to allow 1st order diffraction for green and red laser sources. The green and red solid lines in FIG. 14(b) show the calculated diffraction angle of a 1 μm period grating under strain ranging from −5% to 13% and illuminated with green (λ=543.5 nm) and red (λ=668.3 nm) laser light, respectively. As strain is increased, diffraction is predicted to drop from 35° to 27° for green light and 45° to 34° for red light.

In order to test the performance of the fabricated gratings, the diffraction angle was measured using a setup as depicted in FIG. 14(a). A He—Ne laser (Uniphase 1974P at 543.5 nm) and a diode laser (Thorlabs LDM670 at 668.3 nm) were used to generate coherent green and red light, respectively. The wavelength is crucial for the accuracy of the system and was monitored by a spectrometer. The laser source was directly aimed at transmission grating which was mounted in stretching stage. At a distance of 10 cm past the grating, a semi-transparent paper screen was installed. Behind the screen, a camera (Canon 550D) was placed to capture the images of the diffracted laser beams as they illuminate the screen. The strain was varied from −4% to 12% of strain with 0.25% increments.

Determination of Dominant Laser Wavelength

For an accurate measurement of the diffraction angle, it is crucial to exactly determine the dominant laser wavelength. Therefore, spectroscopy was performed on both lasers used in the experiments. A peak intensity analysis (not shown) revealed that the dominant intensity peaks corresponded to the dominant wavelength of (λ=543.5 nm) for the green He—Ne laser (Uniphase 1974P) and (λ=668.3 nm) for the red diode laser (Thorlabs LDM670).

First Order Diffraction Angle Determination

Images (not shown) of the back of the semi-transparent were taken using a Canon 550d mounted on the optical bench in the optical axis of the laser beam. The reference rings on the screen were calibrated before the measurement to ensure dimensional accuracy. Artefacts were seen around the y-axis on the screen, which are caused by the PDMS surface due to the laser not being focussed on the grating, to ensure a planar wave entering the grating.

The location of the $0^{th}$ and $1^{st}$ order diffracted beams can be identified as bright spots on the screen. The diffraction angle θ can be determined using a trigonometric relation, according to equation (2):

$$\tan(\theta) = \frac{a}{b} \quad \text{(Equation 2)}$$

where a is the distance between the bright spot of $0^{th}$ and $1^{st}$ order diffracted beams on the screen and b is the known distance of the grating to the screen.

Flexible Imaging Array Sensor

A flexible sensor for use in detecting electromagnetic radiation according to another preferred embodiment of the present invention will now be described.[39]

The flexible sensor according to this embodiment takes the form of a flexible imaging array sensor sensitive to ultra-violet (UV) radiation. The flexible imaging array sensor comprises many of the same features as the stretchable oxygen-deficient ZnO-based sensor described in the first preferred embodiment in that it comprises a polymer or elastomer substrate and an oxygen-deficient zinc oxide (ZnO) sensing element applied to the polymer or elastomer substrate. In this embodiment however, the polymer or elastomer of choice is polyimide rather than the stretchable PDMS. By virtue of this arrangement, the flexible imaging array sensor is designed to take advantage of the flexibility of the substrate and the sputter-deposited oxygen-deficient ZnO thin film to realize the creation of a flexible, visible-blind, large area UV imaging sensor in which the sensing plane is curved to mimic the human eye, with the aim of reducing the distortion and chromatic aberration associated with the more rigid planar electronic imaging devices such as CMOS sensors that are typically used in conventional imaging systems.

FIG. 15(a) shows a schematic representation of the flexible oxygen-deficient ZnO-based imaging array sensor (in exploded view) according to this preferred embodiment.

Commercially available copper-cladded polyimide is used as the substrate for the flexible oxygen-deficient ZnO-based imaging array sensor, owing to its high temperature and chemical stability.

As shown in FIG. 15(a), the copper thin film layer on the flexible copper-cladded polyimide substrate is defined as the pair of terminal electrodes using standard lithography technique and wet etching. This layer forms the base of the flexible oxygen-deficient ZnO-based imaging array sensor. The robust copper layer enables the facile interfacing of the sensor as well as integration with existing technology through well-established techniques such as soldering.

The sensing element further comprises a polymer isolation layer comprising a plurality of cavities into which the oxygen-deficient ZnO sensing elements are embedded. The polymer used for the isolation layer is one that can be photo-patterned, such as, for example, polyimide, polymethyl methacrylate (PMMA), photo-patternable epoxy resin, polyethylene terephthalate (PET), and the like.

In this embodiment, the polymer isolation layer is formed using photo-patternable polyimide on account of the desirable mechanical stability of this polymer.

As shown in FIG. 15(a), photo-patternable polyimide is spun on top of the base layer to form a thin film isolation layer that isolates the respective pairs of terminal electrodes. The cured polyimide layer is then photo-patterned to define an opening for a bridge (described below) to connect the now isolated pairs of terminal electrodes and cavities into which the oxygen-deficient ZnO sensing elements will be embedded.

To connect the now-isolated pairs of terminal electrodes with the interfacing pad, an electron beam evaporated gold thin film (250 nm with 100 nm chromium adhesion layer) that offers high electrical conductivity with low film thicknesses. This so-called bridge is formed by standard photo-lithography (FIGS. 15(a) and 15(b)).

The oxygen-deficient ZnO sensing elements are then sputter-deposited on top of the copper electrodes by reactive magnetron sputtering. The oxygen-deficient ZnO sensing elements (referred to as pixels) are patterned by standard photolithography methods and wet etching.

FIG. 15(b) shows a magnified view of a single pixel of the flexible oxygen-deficient ZnO-based imaging array sensor, and FIG. 15(c) shows a photograph of the flexible oxygen-deficient ZnO-based imaging sensor with tinned ports ready for operation.

Detailed information on the fabrication process can be found in the Experimental Section below.

The resulting oxygen-deficient ZnO-based imaging array sensor is 30 µm thick, highly flexible (FIG. 15(c)), and comprises of 256 pixels spread over 57 µm×89 µm with a 2.6 mm pitch.

The atomic concentrations of the zinc and oxygen in the oxygen-deficient ZnO thin film were characterised via X-ray photoelectron spectroscopy (XPS) in order to ascertain the composition of the oxygen-deficient ZnO thin film.

As shown in FIG. 16(a) an X-ray photoelectron spectroscopy (XPS) depth profile of extracted atomic concentrations of zinc and oxygen of the oxygen-deficient ZnO thin film of the imaging array sensor reveals that the oxygen-deficient ZnO thin film has a uniform oxygen deficiency profile throughout the film thickness. Furthermore, the as-deposited films are preferentially (002) oriented as confirmed by X-ray diffraction (not shown).

To validate the suitability of the oxygen-deficient ZnO thin film, the inventors characterised the optical response of a single pixel in detail. In order to analyse the response of a single pixel of the flexible oxygen-deficient ZnO-based imaging array sensor to UV exposure, the single pixel sample was irradiated with UV light (for 10 s) using a 365 nm light emitting diode (LED) normalized to the OFF state (shaded area) with logarithmically increasing UV intensity, 0.5 mW/cm$^2$, 2.1 mW/cm$^2$ and 26.6 mW/cm$^2$. As shown in FIG. 16(b), a strong decrease in resistance is observed under UV exposure. It is also observed that the magnitude of resistance change increases with UV intensity. It should be noted that, the response time of a single pixel is not representative of the performance in an imaging device. The initial response is fast (~30 ms) and provides the majority of the contrast. This is followed by a slow creep to the initial resistance which has a negligible effect on the image, as the pixel is not expected to be unexposed for such a long duration of time.

FIG. 16(c) shows a plot of peak sensitivity ($R/R_0$) vs. incident UV power extracted (mW/cm$^2$) of data extracted from FIG. 16(b). The analysis reveals that the change in resistance is proportional, with a logarithmic dependence, to the surface power density.

As shown in FIG. 16(d), the inventors further characterised the response rate of the single pixel sample to assess its suitability for use in video imaging, which requires a quick response to exposure change to allow for motion-blur-free images. For this purpose, the inventors modulated the frequency (2 Hz to 128 Hz) of UV exposure to the UV LED light source (365 nm at 25 mW/cm$^2$) and acquired the response in situ. The recorded intensity drops slightly as exposure frequency increases. At the peak test frequency of 128 Hz, a reduction in response of 100% can be observed. Firstly, this reduction in sensitivity can be explained by the decrease in incident energy through a shorter exposure time. Secondly, the drop in sensitivity can be ascribed to the inherent sensing mechanism of the oxygen-deficient ZnO thin film that relies on oxygen re-adsorption to recover the ZnO to its initial resistance[34,35]. This process is constantly ongoing and a full recovery of the oxide cannot be achieved in short exposure cycles. However, the rate of re-adsorption varies depending on the surface structure. A higher film roughness facilitates more re-adsorption leading to higher speed and sensitivity as shown previously.[34]

In order to estimate the spectral sensitivity of the ZnO films, the inventors conducted transmission tests on a thin film sputtered on glass, showing absorption between 290 nm to 400 nm (not shown). The results of the UV transmission tests indicated that the spectral sensitivity range is in close agreement with the literature.[36]

In order to verify the spectral sensitivity, which was estimated from the transmission measurement, the inventors used a Thorlabs LED4D007 light source with 4 LED light sources (365 nm, 85 mW, 455 nm, 310 mW, 530 nm, 100 mW, 625 nm, 240 mW) to irradiate a single pixel with multiple wavelengths to test its response.

Figure 17:
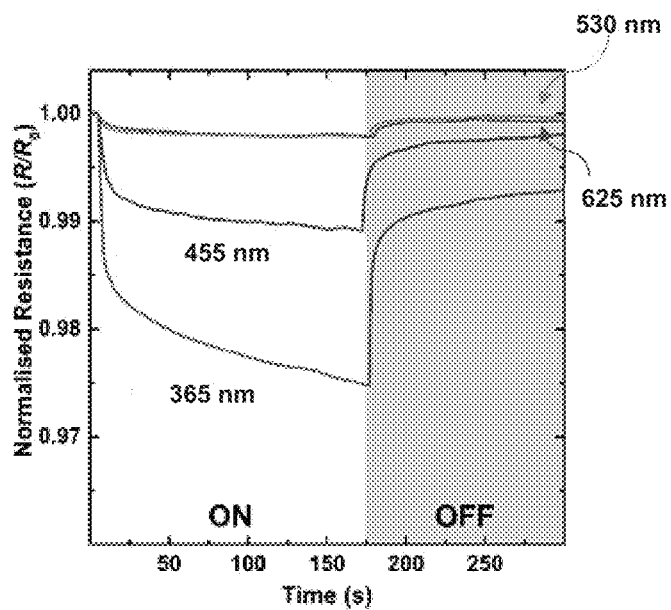
FIG. 17 shows a plot of peak sensitivity ($R/R_0$) response of a single pixel of the imaging array sensor of FIG. 15 when exposed to light sources of different wavelengths (365 nm, 455 nm, 530 nm and 625 nm)

As shown in FIG. 17, a strong response to 365 nm can be observed. The response to the 455 nm can be attributed to the wide spectrum emitted by the deep blue LED (400-500 nm), which falls within the spectral sensitivity of the oxygen-deficient ZnO pixel. The visible colour light sources show negligible response, as expected.

To determine the nature of the Cu/ZnO interface, current-voltage (I-V) characteristics, without and with UV illumination (26.6 mW/cm$^2$), were acquired under a bias sweep from −10 V to 10V.

Figure 18:
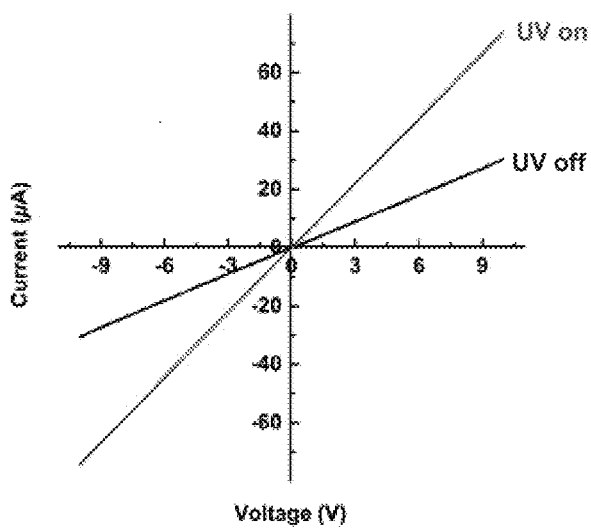
FIG. 18 shows the I-V characteristics of a single pixel of the imaging array sensor of FIG. 15 in its initial (OFF state) and under UV illumination (ON state) with 26.6 mW/cm$^2$ illumination).

As shown in FIG. 18, the I-V analysis confirms the ohmic nature of the Cu/ZnO interface. This allows for a free choice in measurement bias. The single pixel characterisation shows that the oxygen-deficient ZnO thin films allow for high sensing speed and sensitivity. This suggests that the oxygen-deficient ZnO sensing elements are suitable for imaging applications.

Figure 19:
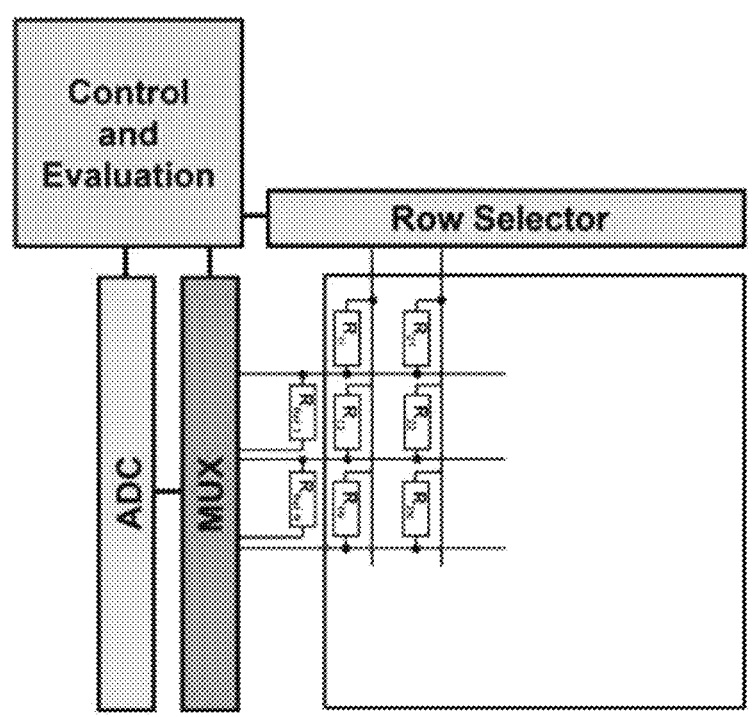
FIG. 19 shows a block diagram representation of the internal electrical connection of the single pixels of the imaging array sensor of FIG. 15 and their connection to peripheral elements.

After ascertaining the suitability of a single ZnO pixel, the inventors characterised an entire array comprising of 256 pixels to evaluate its imaging capabilities. In order to test the array for a real imaging application, the oxygen-deficient ZnO-based imaging array sensor is connected to control and evaluation electronics which is capable of reading 256 pixels of the imaging array in a serial process. This is done by sequentially selecting each row of the array with a subsequent read out of each column via an analogue digital converter (ADC) as shown in the detailed block diagram shown in FIG. 19. A picture is then generated by digitally comparing the exposure reading with a dark calibration. Additional descriptions can be found in the Experimental Section.

Figure 20:
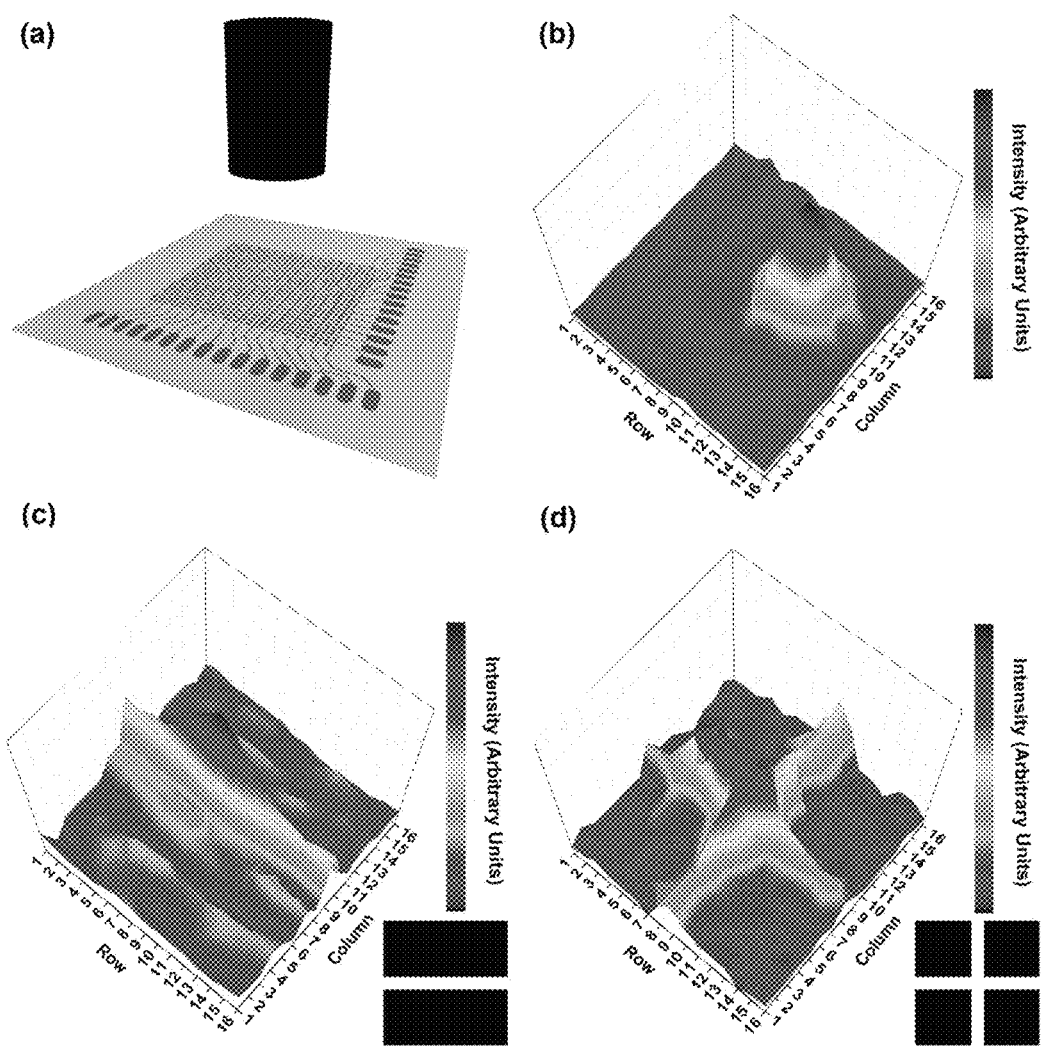
FIG. 20 shows (a) a schematic representation of the test setup for determining the imaging capability of the flexible oxygen-deficient ZnO-based imaging array sensor of FIG. 15 when irradiated using a perpendicularly-mounted UV source (365 nm), and three-dimensional representations of imaging results are presented for high intensity exposure (25 mW/cm$^2$) over a small area in (b) and for medium intensity (10 mW/cm$^2$) exposure through masks, with a single line exposure in (c) and a cross-shaped exposure in (d)

First, the array is mounted on a flat surface as depicted in FIG. 20(a). To test the performance under high radiation intensity and susceptibility to crosstalk, the inventors tested the imaging capability of the array with a high intensity, small area exposure. The test was carried out by irradiating the array with a UV LED source perpendicular to the array at a distance of 1 cm resulting in an intensity of 25 mW/cm$^2$ and an irradiated area of ~1 cm$^2$. The resulting image can be seen in FIG. 20(b). The intensity profile obtained from the array shows a high intensity where the centre of the lamp was placed with a rapidly decaying intensity at the neighbouring pixels. A marginal amount of crosstalk is also observed.

To visualise the characteristic radiation profile of the spot source, and demonstrate the arrays ability to monitor intensities on a two-dimensional plane, a line exposure test was performed. The line accuracy was tested by recording the intensity of a UV LED in FIG. 20(c). The single line of the array was left uncovered the other pixels were blocked using a mask exposing only 1 column of the array. A peak UV intensity of 10 mW/cm$^2$ was chosen by extending the distance between array and source to 5 cm and aimed at the centre of the sensing array. The resulting image shows the characteristic intensity profile of the LED confirming the correct operation of the oxygen-deficient ZnO-based imaging array sensor.

To verify the operation of all columns and rows simultaneously, a cross-shaped exposure was applied to the array by using the above described masking technique. The obtained image (FIG. 20(d)) shows a high centre intensity decaying to the outside of the array, further verifying the functionality of the imaging array.

Figure 21:
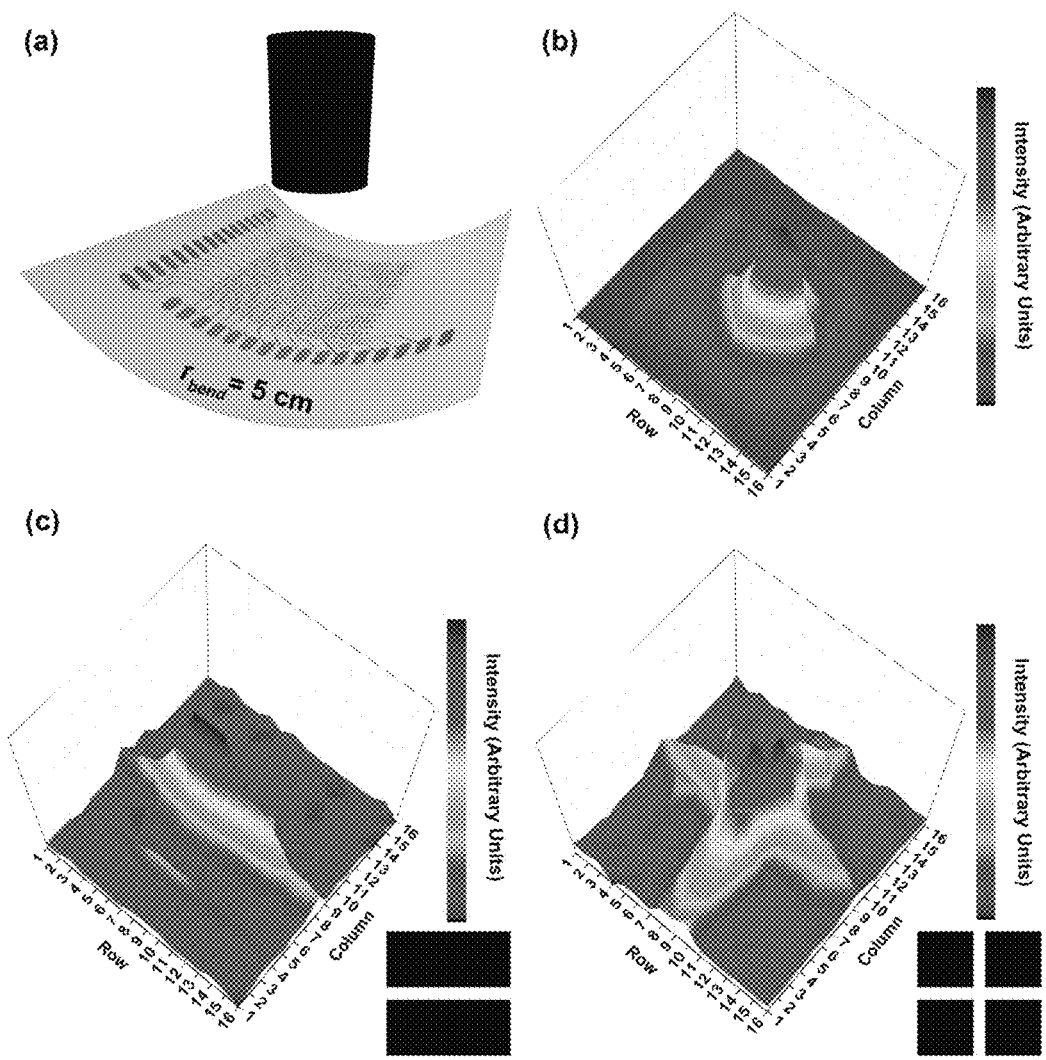
FIG. 21 shows (a) a schematic representation of the test setup for determining the imaging capability of the flexible oxygen-deficient ZnO-based imaging array sensor of FIG. 15 with a concave curvature (bending radius $r_{bend}$ of 5 cm) when irradiated using a perpendicularly-mounted UV source (365 nm), and three-dimensional representation of imaging results are presented for high intensity exposure (25 mW/cm$^2$) over a small area in (b) and for medium intensity (10 mW/cm$^2$) exposure through masks, with a single line exposure in (c) and a cross-shaped exposure in (d)

To explore the tolerance of the imaging array to flexing or bending, the device was mounted on a half-pipe with a radius ($r_{bend}$) of 5 cm as represented in the schematic shown in FIG. 21(a). Subsequently, a high intensity, low area exposure test was performed, analogous to the flat surface experiment. The resulting image shows a high intensity peak with spatially strong decay (FIG. 21(b)). In comparison to the image obtained from the flat mounted sensor (FIG. 20(b) and FIG. 21(b)), no degradation in performance could be observed, as well as little crosstalk. The single column (or line) exposure was also performed. Due to the curvature of the array ($r_{bend}$=5 cm), the source has now an equal distance to the every pixel of the array, and therefore, an altered intensity profile is expected. The obtained image from the array shows a change in intensity profile in comparison to the flat mounted array. The recorded image shows a low intensity towards the edges of the array (FIG. 21(c)). Due to the curvature, a goniometric setup is mimicked, and the spatial illumination profile of the UV LED source is now recorded in situ, capturing the intensity with a constant distance to the source (5 cm). This measurement is consistent with the spatial radiation profile of the LED source mentioned in the datasheet highlighting a possible application for such a bendable array. Again to show all rows and lines in operation, the exposure of a cross-shaped structure was also performed. The obtained image (FIG. 21(d)) shows the anticipated change in intensity profile when compared to the flat mounted surface.

Figure 22:
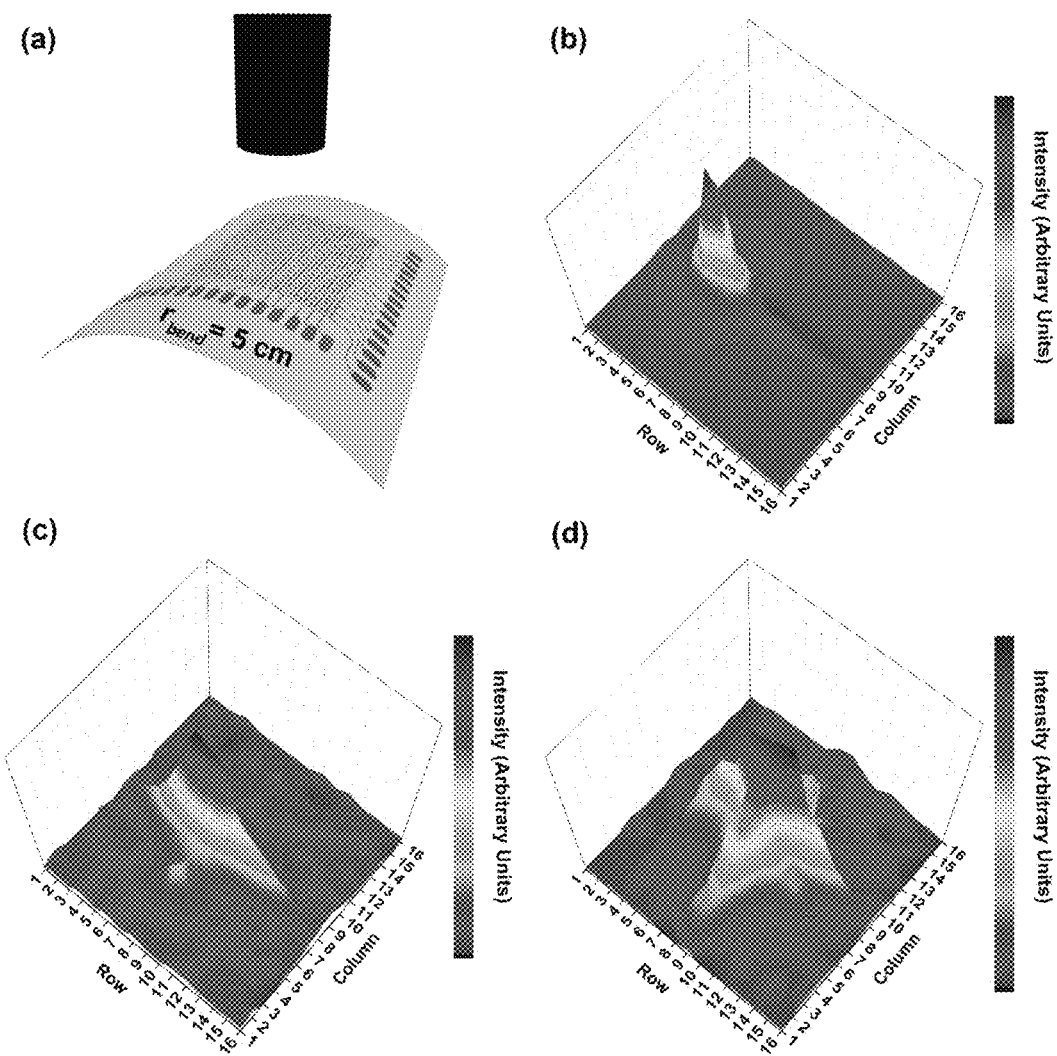
FIG. 22 shows (a) a schematic representation of the test setup for determining the imaging capability of the flexible oxygen-deficient ZnO-based imaging array sensor of FIG. 15 with a convex curvature (bending radius $r_{bend}$ of 5 cm) when irradiated using a perpendicularly-mounted UV source (365 nm), and three-dimensional representation of imaging results are presented for high intensity exposure (25 mW/cm$^2$) over a small area in (b) and for medium intensity (10 mW/cm$^2$) exposure through masks, with a single line exposure in (c) and a cross-shaped exposure in (d).

As shown in FIG. 22, the functionality of the array was also tested for the opposite, convex curvature ($r_{bend}$=5 cm) with no performance deterioration. These results highlight the stable performance of the imaging array even under considerable curvature.

Device Failure Analysis Via In Situ Electron Microscopy

Additional evidence towards the mechanical durability of the flexible oxygen-deficient ZnO-based imaging array sensor was obtained via in situ electron microscopy where strain is applied to the oxygen-deficient ZnO coated polyimide substrate. No alterations in the film morphology were observed up to a strain of 2%. Under a strain of 4% (which is also the elastic limit of polyimide), the inventors observed the onset of micro-cracking which still does not result in the failure of the oxygen-deficient ZnO thin film but only in a temporary increase of resistance.[37] A subsequent increase in strain deforms the flexible oxygen-deficient ZnO-based imaging array sensor permanently due to plastic deformation in the polyimide substrate which results in a marginal increase in micro-cracking. However, no delamination of the oxygen-deficient ZnO thin film is observed.

CONCLUSION

A visible-blind UV sensing array has been successfully fabricated using an oxygen-deficient ZnO thin film. Single pixel characterisation was undertaken to evaluate sensitivity and response of the ZnO sensing elements. The functionality of the imaging device has been shown in flat (FIG. 20), concave (FIG. 21), and convex (FIG. 22) states. No degradation in performance was observed. The imaging sensor showed dimensional accuracy as well as accurate intensity profiles of a single point source in flat and bent states. Furthermore, it can be used to record point source radiation patterns. These results highlight the advanced capabilities of such a flexible imaging sensor, allowing incorporation in non-planar geometries. The inventors believe that this functionality can pave the way for low complexity, high efficiency devices enabling applications such as in situ monitoring of industrial equipment, lithography flame detection, environmental studies, medical and communication equipment.

Experimental Section—Flexible Imaging Array Sensor

Device Fabrication

The fabrication of the flexible oxygen-deficient ZnO-based imaging array sensor starts with the preparation of the temporary carrier for the flexible substrate. For this purpose, a 4 inch silicon wafer is coated with a thin layer of polydimethylsiloxane (PDMS) ~20 μm thick, synthesized by spin coating with a spin speed of 1500 rpm for 30 s. The elastomeric material is then cured at room temperature for 24 h. Commercially available polyimide substrate (25 μm thick with 9 μm copper thickness, Pyralux AP 7163E, DuPont) which is coated with 2 μm electroplated copper is then laminated to the temporary carrier and trimmed. The substrate is now compatible with standard micro-fabrication techniques. A layer of AZ4562 resist is then applied via spin coating to form a 10 μm thick layer followed by a 200 mW/cm² UV exposure through a mask, which defines the first electrode layer and contact patch with subsequent development in AZ400K developer.

Subsequently, the substrate is temporarily delaminated from the carrier to undergo a wet chemical etching step in an 80° C. hydrogen peroxide solution for 3 min, completing the definition for the first electrode layer. The photoresist is then stripped in acetone, followed by an isopropanol rinse (FIG. 15(a)). The flexible electrodes are then affixed to the PDMS carrier via lamination.

A 5 μm thick photo-patternable polyimide (HD8820, HD Microsystems) isolation layer is then synthesised via spin coating at 3,500 rpm for 30 s. A subsequent exposure through a transparency mask then defines the opening for the bridge and sensing elements. The photo-patternable polyimide, is then developed in AZ 356MIF followed by a deionised water rinse (FIG. 15(a)). The polyimide thin film is then cured in a nitrogen environment for 1 h at 350° C.

The bridge is then defined via lift off technique using AZ4562 with prior described parameters and a subsequent e-beam evaporation of 100 nm Cr and 250 nm Au followed by stripping in acetone facilitated by ultra-sonic agitation.

The flexible electrodes are now completed and ready for the synthesis of the oxygen-deficient ZnO sensing layer via reactive magnetron sputtering. The deposition takes place at 200 W with 5 mTorr process pressure in an Ar:$O_2$ (15%: 85%) atmosphere. With a process substrate temperature of 250° C. and 2 h deposition, 200 nm thick layers are obtained. The oxygen-deficient ZnO layer is then patterned using AZ4562 with above-described synthesis parameter and subsequent etching in 30% hydrochloric acid for 3 s. The flexible oxygen-deficient ZnO-based imaging array sensor is now delaminated from the carrier and connected to the evaluation electronics via soldering.

Evaluation and Control Electronics

In order to read out the imaging array, a National instruments (NI) cDAQ-9174 system with a NI 9205 32-channel analog voltage input module was used. The signal was read out of each row in differential mode. The differential mode allows for a common mode noise suppression, and therefore, boosts signal-to-noise ratios allowing for a better imaging performance. For the channel selection, a NI 9264 16-Channel analog output was used. The hardware was controlled with a tailored LabVIEW code. This allows for a flexible gain of the system which can be tailored to the application.

In this work, it is fixed to 10 V to achieve a high sensitivity. The resistive elements are connected according to the schematic shown in FIG. 19. The resistors in each row are in series with an individual reference resistor, forming a voltage divider, which is shared for each column in the array. The reference resistor is connected to a multiplexer (MUX) which allows for a differential voltage measurement across each reference resistor in a sequential manner. The differential measurement, if not active is switched to high impedance. In practice the measurement is carried out in the following manner: Row 1 is biased by the row selector. Now the sequential read out of the column starts with $R_{ref\_1}$ through to $R_{ref\_16}$. Subsequently all 16 rows are selected and the column read out to is carried out to read in all elements of the array. The signal gathered from each element is saved in an array and digitally compared against a prior recorded dark reference to compile the image. The resistive elements of the array were read in via a row-by-row selection. Each row was read out in series via a voltage divider with an external reference resistor. The signal was then digitally compared against a prior recorded dark reference to compile the image.

Optical Testing

The optical evaluation was carried out with a UV light emitting diode (LED) (PowerStar S5050) with a peak wavelength of 365 nm. The LED was powered by a Recom constant current source. The surface power density was adjusted by the source-detector distance and verified by a Karl Suss power meter. For the speed-dependent sensing experiments, the light source was modulated via a dimming port of the constant current source. The modulation signal was generated by a function generator.

Advantages

From the foregoing discussion, it should be apparent to a skilled person in the art that the flexible and stretchable oxygen-deficient ZnO-based sensors of the present invention provide many advantages over their existing rigid counterparts.

For instance, the introduction of a distinctive microtectonic effect enabled oxygen-deficient, nano-patterned zinc oxide (ZnO) thin film on a biocompatible elastomeric substrate enables the realization of large area, stretchable, transparent, and ultra-portable sensors, where the functional oxide is itself stretchable, thereby enabling the stretchable sensors to outperform their rigid counterparts under room temperature conditions.

The stretchable oxygen-deficient ZnO-based gas sensor demonstrated above is able to sense hazardous environments (explosive pollutant and toxic gases such as $H_2$ and $NO_2$ gases even at extremely low concentrations) that can occur in domestic or industrial settings.

The stretchable oxygen-deficient ZnO-based UV sensor demonstrated above can be harnessed to detect the most harmful type of UV light which can prove crucial for the prevention of skin aging, eye damage, and skin cancer.

It is also demonstrated that nanoscale ZnO diffraction elements embedded within an elastomeric matrix can function as tunable diffraction gratings, capable of sensing displacements with nanometer accuracy.

The flexible oxygen-deficient ZnO-based imaging array demonstrated above shows that the sensitivity and response of the oxygen-deficient ZnO sensing elements is not affected by the degree of bending employed. By virtue of these results, it is clear that this flexible oxygen-deficient ZnO-based imaging array may be employed in non-planar geometries, thereby paving the way for low complexity, high efficiency devices enabling applications such as in situ monitoring of industrial equipment, lithography flame detection, environmental studies, medical and communication equipment.

By virtue of employing a synthesis strategy in which the ZnO sensing elements are grown with controlled oxygen-deficiency, resulting in a higher carrier concentration, and therefore a lower resistance, this allows for the use of standard digital electronics compatible measurement set up, ultimately allowing for a flexible device with higher degree of integration. This strategy also avoids complex synthesis routes such as doping and increases carrier concentration upon UV exposure, towards enhanced sensitivity under standard temperature and pressure.

Such transparent, and flexible or stretchable oxygen-deficient ZnO-based sensors offer significant potential for the development of cost-effective, bio-compatible, functional, and curvilinear electronic and optoelectronic devices. Furthermore, a precise control over spatial resolution in the nanometer regime is believed will allow for applications such as oxide-based gratings, which exhibit high accuracy and can track surface movements of PDMS down to sub-10 nm resolution.

In short, the inventors have demonstrated that the incorporation of electronic materials, in particular functional metal oxides onto mechanically conformal platforms offers a new pathway for the development of sophisticated, stretchable electronic devices that can be bent, stretched, twisted, and folded into complex curvilinear shapes while maintaining their electronic characteristics, performance, and reliability. This new class of electronics is promising for designing novel systems, such as in vitro pH sensors,[8] transient[9] and printable electronic devices,[38] sensory robotic skin, and wearable electronic devices.

REFERENCES

[1] G. Gustafsson, Y. Cao, G. Treacy, F. Klavetter, N. Colaneri, A. Heeger, *Nature* 1992, 357, 477.
[2] G. H. Gelinck, H. E. A. Huitema, E. van Veenendaal, E. Cantatore, L. Schrijnemakers, J. B. van der Putten, T. C. Geuns, M. Beenhakkers, J. B. Giesbers, B.-H. Huisman, *Nature materials* 2004, 3, 106.
[3] I. Yagi, N. Hirai, Y. Miyamoto, M. Noda, A. Imaoka, N. Yoneya, K. Nomoto, J. Kasahara, A. Yumoto, T. Urabe, *Journal of the Society for Information Display* 2008, 16,
[4] L. Sun, G. Qin, J. H. Seo, G. K. Celler, W. Zhou, Z. Ma, *Small* 2010, 6, 2553.
[5] J. Kim, A. Banks, H. Cheng, Z. Xie, S. Xu, K. I. Jang, J. W. Lee, Z. Liu, P. Gutruf, X. Huang, *Small* 2014, 11, 906.
[6] M. C. McAlpine, H. Ahmad, D. Wang, J. R. Heath, *Nature materials* 2007, 6, 379.
[7] G. Sberveglieri, *Sensors and Actuators B: Chemical* 1995, 23, 103.
[8] H. J. Chung, M. S. Sulkin, J. S. Kim, C. Goudeseune, H. Y. Chao, J. W. Song, S. Y. Yang, Y. Y. Hsu, R. Ghaffari, I. R. Efimov, *Advanced healthcare materials* 2014, 3, 59.
[9] S.-W. Hwang, H. Tao, D.-H. Kim, H. Cheng, J.-K. Song, E. Rill, M. A. Brenckle, B. Panilaitis, S. M. Won, Y.-S. Kim, *Science* 2012, 337, 1640.
[10] S. Walia, S. Balendhran, H. Nili, S. Zhuiykov, G. Rosengarten, Q. H. Wang, M. Bhaskaran, S. Sriram, M. S. Strano, K. Kalantar-zadeh, *Progress in Materials Science* 2013, 58, 1443.
[11] P. Gutruf, C. M. Shah, S. Walia, H. Nili, A. S. Zoolfakar, C. Karnutsch, K. Kalantar-zadeh, S. Sriram, M. Bhaskaran, *NPG Asia Materials* 2013, 5, e62.

[12] K. Ellmer, Journal of Physics D: Applied Physics 2000, 33, R17.
[13] G. Xiong, J. Wilkinson, B. Mischuck, S. Tüzemen, K. B. Ucer, R. T. Williams, *Applied Physics Letters* 2002, 80, 1195.
[14] M. Breedon, M. Spencer, I. Yarovsky, *The Journal of Physical Chemistry C* 2010, 114, 16603.
[15] M. Nyberg, M. A. Nygren, L. G. Pettersson, D. H. Gay, A. L. Rohl, *The Journal of Physical Chemistry* 1996, 100, 9054.
[16] H.-T. Wang, B. Kang, F. Ren, L. Tien, P. Sadik, D. Norton, S. Pearton, J. Lin, *Applied Physics Letters* 2005, 86, 243503.
[17] S. T. Shishiyanu, T. S. Shishiyanu, O. I. Lupan, *Sensors and Actuators B: Chemical* 2005, 107, 379.
[18] G. Hu, R. Zhou, R. Yu, L. Dong, C. Pan, Z. L. Wang, *Nano Research* 2014, 7, 1083.
[19] R. Zhou, G. Hu, R. Yu, C. Pan, Z. L. Wang, *Nano Energy* 2015, 12, 588.
[20] C. Pan, R. Yu, S. Niu, G. Zhu, Z. L. Wang, *ACS nano* 2013, 7, 1803.
[21] R. Yu, C. Pan, Y. Hu, L. Li, H. Liu, W. Liu, S. Chua, D. Chi, Z. L. Wang, *Nano Research* 2013, 6, 758.
[22] J. H. Jun, H. Seong, K. Cho, B.-M. Moon, S. Kim, *Ceramics International* 2009, 35, 2797.
[23] C. Soci, A. Zhang, B. Xiang, S. A. Dayeh, D. Aplin, J. Park, X. Bao, Y.-H. Lo, D. Wang, *Nano letters* 2007, 7, 1003.
[24] P. Lin, X. Yan, Z. Zhang, Y. Shen, Y. Zhao, Z. Bai, Y. Zhang, *ACS applied materials & interfaces* 2013, 5, 3671.
[25] R. Ghosh, D. Basak, S. Fujihara, *Journal of Applied Physics* 2004, 96, 2689.
[26] A. Becheri, M. Durr, P. L. Nostro, P. Baglioni, *Journal of Nanoparticle Research* 2008, 10, 679.
[27] A. M. Vengsarkar, P. J. Lemaire, J. B. Judkins, V. Bhatia, T. Erdogan, J. E. Sipe, *Lightwave Technology, Journal of* 1996, 14, 58.
[28] G. D. Goodno, G. Dadusc, R. Miller, *JOSA B* 1998, 15, 1791.
[29] T. Ma, H. Liang, G. Chen, B. Poon, H. Jiang, H. Yu, *Opt. Express* 2013, 21, 11994.
[30] Kappertz, O., Drese, R., Ngaruiya, J. M. & Wuttig, M. Reactive sputter deposition of zinc oxide: Employing resputtering effects to tailor film properties. *Thin Solid Films* 484, 64-67 (2005).
[31] Zhang, D. et al. Properties of ZnO thin films deposited by DC reactive magnetron sputtering under different plasma power. *Appl. Phys. A* 97, 437-441 (2009).
[32] Xu, Y., Goto, M., Kato, R., Tanaka, Y. & Kagawa, Y. Thermal conductivity of ZnO thin film produced by reactive sputtering. *Journal of Applied Physics* 111, 084320 (2012).
[33] R. Lefever, Review of Scientific Instruments 1962, 33, 1470.
[34] P. Gutruf, E. Zeller, S. Walia, H. Nili, S. Sriram, M. Bhaskaran, *Small* 2015, 11, 4532-4539.
[35] K. Liu, M. Sakurai, M. Aono, *Sensors* 2010, 10, 8604-34.
[36] Y. Liu, C. Gorla, S. Liang, N. Emanetoglu, Y. Lu, H. Shen, M. Wraback, *Journal of Electronic Materials* 2000, 29, 69-74.
[37] P. Gutruf, S. Walia, M. N. Ali, S. Sriram, M. Bhaskaran, *Applied Physics Letters* 2014, 104, 021908.
[38] H. Yan, Z. Chen, Y. Zheng, C. Newman, J. R. Quinn, F. Dötz, M. Kastler, A. Facchetti, *Nature* 2009, 457, 679.
[39] P. Gutruf. S. Walia, S. Siriam, M. Bhaskaran, *Advanced Electronic Materials,* 2015, 1, 1500264.

Whenever a range is given in the specification, for example, a temperature range, a time range, or concentration range, all intermediate ranges and subranges, as well as all individual values included in the ranges given are intended to be included in the disclosure. It will be understood that any subranges or individual values in a range or subrange that are included in the description herein can be excluded from the claims herein.

All definitions, as defined and used herein, should be understood to control over dictionary definitions, definitions in documents incorporated by reference, and/or ordinary meanings of the defined terms.

The indefinite articles "a" and "an," as used herein in the specification, unless clearly indicated to the contrary, should be understood to mean "at least one."

The phrase "and/or," as used herein in the specification, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

While the invention has been described in conjunction with a limited number of embodiments, it will be appreciated by those skilled in the art that many alternatives, modifications and variations in light of the foregoing description are possible. Accordingly, the present invention is intended to embrace all such alternatives, modifications and variations as may fall within the spirit and scope of the invention as disclosed.

Where the terms "comprise", "comprises", "comprised" or "comprising" are used in this specification (including the claims) they are to be interpreted as specifying the presence of the stated features, integers, steps or components, but not precluding the presence of one or more other features, integers, steps or components, or group thereof.

The claims defining the invention are as follows:

1. A flexible or stretchable sensor for use in detecting a substance and/or electromagnetic radiation, the sensor comprising:
    a flexible or stretchable substrate;
    a pair of terminal electrodes disposed on the flexible or stretchable substrate in mutually spaced apart and opposing relation; and
    a sensing element applied to the flexible or stretchable substrate, between and in electrical contact with the pair of terminal electrodes, wherein the sensing element is responsive to a substance and/or electromagnetic radiation impinging thereon, and wherein when a voltage is applied across the sensor, an electrical signal is generated that is proportional to a resistance value corresponding to a sensing of the substance and/or electromagnetic radiation impinging on the sensing element,
wherein the sensing element comprises an oxygen-deficient metal oxide thin film layer.

2. A sensor according to claim 1, wherein the oxygen-deficient metal oxide thin film layer of the sensing element defines a sensor surface oriented for contact with the substance and/or electromagnetic radiation in use.

3. A sensor according to claim 2, wherein the sensor surface of the oxygen deficient metal oxide layer comprises a micro-tectonic plate-like structure.

4. A sensor according to claim 3, wherein the micro-tectonic plate-like structure allows the oxygen-deficient metal oxide layer to flex or stretch when the sensor is subject to an applied force.

5. A sensor according to claim 2, wherein the sensor surface of the oxygen deficient metal oxide layer has an average surface roughness that falls within a range of about 40 nm to about 170 nm.

6. A sensor according to claim 2, wherein the oxygen-deficient metal oxide layer is formed from a metal oxide selected from the group consisting of zinc oxide (ZnO), indium tin oxide (ITO), tin oxide and titanium dioxide.

7. A sensor according to claim 2, wherein the oxygen-deficient metal oxide layer has a thickness that falls within a range of about 10 nm to about 1 μm.

8. A sensor according to claim 2, wherein the sensing element further comprises a polymer isolation layer comprising a plurality of cavities into which the oxygen deficient metal oxide layer is embedded.

9. A sensor according to claim 8, wherein the polymer isolation layer is selected from the group consisting of polyimide (PI), polymethyl methacrylate (PMMA), photo-patternable epoxy resin and polyethylene terephthalate (PET).

10. A sensor according to claim 1, wherein the flexible or stretchable substrate comprises a polymer or elastomer.

11. A sensor according to claim 10, wherein the polymer or elastomer is selected from the group consisting of polydimethylsiloxane (PDMS), polyimide (PI) and polyethylene terephthalate (PET).

12. A sensor according to claim 10, wherein the polymer or elastomer is a bioinert or biocompatible material.

13. A sensor according to claim 10, wherein the polymer or elastomer is a gas permeable material.

14. A sensor according to claim 10, wherein the polymer or elastomer has a thickness that falls within a range of about 10 μm to about 500 μm.

15. A sensor according to claim 1, wherein the sensing element is caused to flex or stretch when the sensor is subject to an applied force.

16. A sensor according to claim 15, wherein the applied force is selected from the group consisting of a stretching force, a compressive force, a twisting force and a bending force.

17. A sensor according to claim 16, wherein the force applied to the sensor in use falls within a range of about −5% to about 15% of strain.

18. A sensor according to claim 1, wherein the substance detected by the sensing element is a gas or a liquid.

19. A sensor according to claim 1, wherein the substance detected by the sensing element is a gas selected from the group consisting of $H_2$, $NO_2$, $SF_6$ and $C_4H_{10}$.

20. A sensor according to claim 19, wherein the gas detected by the sensing element is $H_2$ with a sensitivity to $H_2$ concentrations of less than 1% $H_2$ in an air balance with a flow rate of 200 sccm.

21. A sensor according to claim 19, wherein the gas detected by the sensing element is $NO_2$ with a sensitivity to $NO_2$ concentrations of less than 9.9 parts per million in zero air at a flow rate of 200 sccm.

22. A sensor according to claim 1, wherein the substance detected by the sensing element is a liquid selected from the group consisting of gasoline and $C_2H_5OH$.

23. A sensor according to claim 1, wherein the substance or electromagnetic radiation detected by the sensing element is detected at a temperature that falls within a range of 20 degrees Centigrade to 50 degrees Centigrade.

24. A sensor according to claim 1, wherein the electromagnetic radiation detected by the sensing element has a wavelength that falls within a range of 200 nm to 400 nm.

25. A method of sensing a substance and/or electromagnetic radiation using a sensor, the method comprising the steps of:
    a) contacting a sensing element of a flexible or stretchable sensor according to claim 1 with a substance and/or electromagnetic radiation;
    b) applying a voltage across the sensor; and
    c) detecting an electrical signal generated that is proportional to a resistance value corresponding to a sensing of the substance and/or electromagnetic radiation impinging on the sensing element.

26. A method according to claim 25, wherein the sensing element is caused to flex or stretch when the sensor is subject to an applied force.

27. A method according to claim 26, wherein the applied force is selected from the group consisting of a stretching force, a compressive force, a twisting force and a bending force.

28. A method according to claim 26, wherein the force applied to the sensor in use falls within a range of about 4% to about 15% of strain.

29. A method according to claim 25, wherein the substance detected by the sensing element is a gas or a liquid.

30. A method according to claim 29, wherein the gas is selected from the group consisting of $H_2$ and $NO_2$, $SF_6$ and $C_4H_{10}$.

31. A method according to claim 29, wherein the gas detected by the sensing element is $H_2$ with a sensitivity to 1% $H_2$ in an air balance with a flow rate of 200 sccm.

32. A method according to claim 29, wherein the gas detected by the sensing element is $NO_2$ with a sensitivity to $NO_2$ concentrations of less than 9.9 parts per million in zero air at a flow rate of 200 sccm.

33. A method according to claim 25, wherein the substance detected by the sensing element is a liquid selected from the group consisting of gasoline and $C_2H_5OH$.

34. A method according to claim 25, wherein the electromagnetic radiation detected by the sensing element has a wavelength that falls within a range of 200 nm to 400 nm.

35. A method according to claim 25, wherein one or more of steps a) to c) is conducted at a temperature that falls within a range of 20 degrees Centigrade to 50 degrees Centigrade.

* * * * *